(12) United States Patent
Bouchard et al.

(10) Patent No.: US 6,331,635 B1
(45) Date of Patent: *Dec. 18, 2001

(54) TAXOIDS, THEIR PREPARATION AND PHARMACEUTICAL COMPOSITIONS CONTAINING THEM

(75) Inventors: Hervé Bouchard, Ivry-sur-Seine; Jean-Dominique Bourzat, Vincennes; Alain Commerçon, Vitry-sur-Seine, all of (FR)

(73) Assignee: Aventis Pharma S.A., Antony (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/066,929

(22) Filed: Apr. 28, 1998

Related U.S. Application Data

(63) Continuation of application No. 08/622,011, filed on Mar. 26, 1996, now Pat. No. 5,847,170.

(30) Foreign Application Priority Data

Mar. 27, 1995 (FR) .................................. 95 03545
Dec. 22, 1995 (FR) .................................. 95 15381

(51) Int. Cl.⁷ ...................... C07D 263/06; C07D 305/14
(52) U.S. Cl. ......................... 548/215; 549/60; 549/472; 549/473; 549/510; 549/511
(58) Field of Search .................................. 549/510, 511, 549/60, 472, 473; 548/215

(56) References Cited

U.S. PATENT DOCUMENTS

| | | | |
|---|---|---|---|
| 5,229,526 | 7/1993 | Holton | 549/213 |
| 5,319,112 | 6/1994 | Kingston et al. | 549/510 |
| 5,489,601 | 2/1996 | Holton et al. | 514/337 |
| 5,739,362 | 4/1998 | Holton et al. | 549/510 |

FOREIGN PATENT DOCUMENTS

| | | |
|---|---|---|
| 0 336 841 | 10/1989 | (EP) . |
| 0 604 910 | 7/1994 | (EP) . |
| 0 639 577 | 2/1995 | (EP) . |
| 0 694 539 | 1/1996 | (EP) . |
| WO 92/09589 | 6/1992 | (WO) . |
| WO 94/07878 | 4/1994 | (WO) . |
| WO 94/18164 | 8/1994 | (WO) . |
| WO 96/00724 | 1/1996 | (WO) . |

OTHER PUBLICATIONS

Michael L. Shelanski et al., "Microtubule Assembly in the Absence of Added Nucleotides", vol. 70, No. 3, pp. 765–768 (Mar. 1973).

de Gérard Chauviére et al., "Comptes Rendus Des Séances de L'Académie des Sciences", pp. 501–503 (Oct. 1981).

Joydeep Kant et al., "A Chemoselective Approach to Functionalize the C–10 Position of 10–Deacetylbaccatin III Synthesis and Biological Properties of Novel C–10 Taxol® Analogues", Bristol Myers Squibb Pharmaceutical Research Institute, vol. 35, No. 31, pp. 5543–5546 (Jun. 1994).

Theodora W. Greene, "Protective Groups in Organic Synthesis", *Wiley–Interscience Publication*, pp. 50–62 (1981).

Shu–Hui Chen et al., "Paclitaxel Structure–Activity Relationships and Core Skeletal Rearrangements", Central Chemistry, Bristol–Myers Squibb, Chapter 18, pp. 247–261 (Oct. 1994).

D.G.I. Kingston et al., "Progress in the Chemistry of Organic Natural Products", Springer–Verlag, pp. 62–81 (1993).

*Primary Examiner*—Ba K. Trinh
(74) *Attorney, Agent, or Firm*—Finnegan, Henderson, Farabow, Garrett & Dunner, L.L.P.

(57) ABSTRACT

New taxoids of general formula (I):

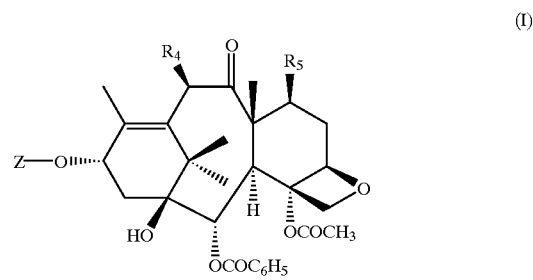

(I)

their preparation and pharmaceutical compositions containing them.

The new products of general formula (I) in which Z represents a radical of general formula (II):

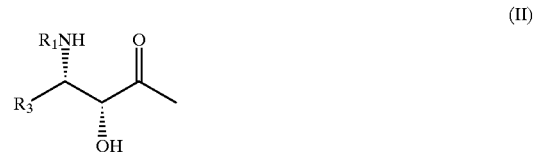

(II)

display noteworthy antitumour and antileukaemic properties.

25 Claims, No Drawings

TAXOIDS, THEIR PREPARATION AND PHARMACEUTICAL COMPOSITIONS CONTAINING THEM

This is a continuation of application Ser. No. 08/622,011, filed Mar. 26, 1996 now U.S. Pat. No. 5,847,170.

The present invention relates to new taxoids of general formula (I)

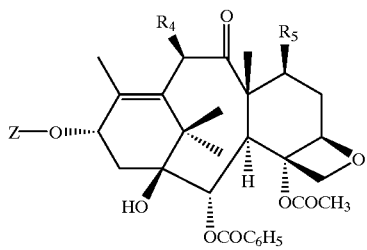

in which:

Z represents a hydrogen atom or a radical of general formula (II):

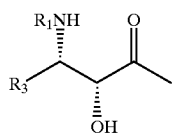

in which:

$R_1$ represents a benzoyl radical optionally substituted with one or more identical or different atoms or radicals selected from halogen atoms, alkyl radicals containing 1 to 4 carbon atoms, alkoxy radicals containing 1 to 4 carbon atoms and trifluoromethyl radicals, a thenoyl or furoyl radical or a radical $R_2$—O—CO— in which $R_2$ represents:
  an alkyl radical containing 1 to 8 carbon atoms,
  an alkenyl radical containing 2 to 8 carbon atoms,
  an alkynyl radical containing 3 to 8 carbon atoms,
  a cycloalkyl radical containing 3 to 6 carbon atoms,
  a cycloalkenyl radical containing 4 to 6 carbon atoms or
  a bicycloalkyl radical containing 7 to 10 carbon atoms, these radicals being optionally substituted with one or more substituents selected from halogen atoms, hydroxyl radicals, alkoxy radicals containing 1 to 4 carbon atoms, dialkylamino radicals in which each alkyl portion contains 1 to 4 carbon atoms, piperidino radicals, morpholino radicals, 1-piperazinyl radicals, said piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycyloalkenyl radicals containing 4 to 6 carbon atoms, phenyl radicals, said phenyl radicals being optionally substituted with one or more atoms or radicals selected from halogen atoms, alkyl radicals containing 1 to 4 carbon atoms, and alkoxy radicals containing 1 to 4 carbon atoms, cyano radicals, carboxyl radicals and alkoxycarbonyl radicals in which the alkyl portion contains 1 to 4 carbon atoms, a phenyl or α- or β-naphthyl radical optionally substituted with one or more atoms or radicals selected from halogen atoms, alkyl radicals containing 1 to 4 carbon atoms, and alkoxy radicals containing 1 to 4 carbon atoms, a 5-membered aromatic heterocyclic radical preferably selected from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, and trifluoromethyl radicals, or a 5-membered aromatic heterocycle containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the understanding that, in the substituents of the phenyl, α- or β-naphthyl and aromatic heterocyclic radicals, the alkyl radicals and the alkyl portions of the other radicals contain 1 to 4 carbon atoms, the alkenyl and alkynyl radicals contain 2 to 8 carbon atoms, and the aryl radicals are phenyl or α- or β-naphthyl radicals, $R_4$ represents an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms or a cycloalkenyloxy radical containing 4 to 6 carbon atoms, these radicals being optionally substituted with one or more substituents selected from halogen atoms, an alkoxy radical containing 1 to 4 carbon atoms, an alkylthio radical containing 1 to 4 carbon atoms, a carboxyl radical, an alkyloxycarbonyl radical in which the alkyl portion contains 1 to 4 carbon atoms, a cyano radical, a carbamoyl radical, an N-alkylcarbamoyl radical and a N,N-dialkylcarbamoyl radical in which each alkyl portion contains 1 to 4 carbon atoms, or both alkyl portions, together with the nitrogen atom to which they are linked, form a saturated 5- or 6-membered heterocyclic radical optionally containing a second hetero atom selected from oxygen, sulphur and nitrogen atoms, said saturated 5- or 6-membered heterocyclic radical optionally being substituted with a substituent selected from an alkyl radical containing 1 to 4 carbon atoms, a phenyl radical, and a phenylalkyl radical in which the alkyl portion contains 1 to 4 carbon atoms, $R_5$ represents an alkoxy radical containing 1 to 6 carbon atoms in an unbranched or branched chain, an alkenyloxy radical containing 3 to 6 carbon atoms, an alkynyloxy radical containing 3 to 6 carbon atoms, a cycloalkyloxy radical containing 3 to 6 carbon atoms or a cycloalkenyloxy radical containing 3 to 6 carbon atoms, these radicals being optionally substituted with at least one substituent selected from halogen atoms, an alkoxy radical containing 1 to 4 carbon atoms, an alkylthio radical containing 2 to 4 carbon atoms, a carboxyl radical, an alkyloxycarbonyl radical in which the alkyl portion contains 1 to 4 carbon atoms, a cyano radical, a carbamoyl radical, an N-alkylcarbamoyl radical, and a N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom selected from oxygen, sulphur and nitrogen atoms, optionally selected with a substituent selected from an alkyl radical containing 1 to 4 carbon atoms, a phenyl radical and a phenylalkyl radical in which the alkyl portion contains 1 to 4 carbon atoms.

Preferably, the aryl radicals which can be represented by $R_3$ are phenyl or α- or β-naphthyl radicals optionally substituted with one or more atoms or radicals selected from halogen atoms (fluorine, chlorine, bromine, iodine) alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5-membered aromatic heterocyclic radicals containing one or more identical or different atoms selected from nitrogen, oxygen and sulphur atoms, optionally substituted with one or more identical or different substituents selected from halogen atoms (fluorine, chlorine, bromine, iodine), alkyl radicals containing 1 to 4 carbon atoms, aryl radicals containing 6 or 10 carbon atoms, alkoxy radicals containing 1 to 4 carbon atoms, aryloxy radicals containing 6 to 10 carbon atoms, amino radicals alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 or 10 carbon atoms, cyano radicals, carboxyl radicals, carbamoyl radicals, alkylcarbamoyl radicals in which the alkyl portion contains 1 to 4 carbon atoms, dialkylcarbamoyl radicals in which each alkyl portion contains 1 to 4 carbon atoms, and alkoxycarbonyl radicals in which the alkoxy portion contains 1 to 4 carbon atoms.

Preferably, the radicals $R_4$ and $R_5$, which may be identical or different, represent unbranched or branched alkoxy radicals containing 1 to 6 carbon atoms, optionally substituted with a methoxy, ethoxy, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl or N-piperidinocarbonyl radical.

More particularly, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals selected from from halogen atoms (fluorine, chlorine), alkyl (methyl), alkoxy (methoxy), dialkylamino (dimethylamino), acylamino (acetylamino), alkoxycarbonylamino (tert-butoxycarbonylamino), trifluoromethyl, a 2-furyl radical, a 3-furyl radical, a 2-thienyl radical, a 3-thienyl radical, a 2-thiazolyl radical, a 4-thiazolyl radical, and a 5-thiazolyl radical, and $R_4$ and $R_5$, which may be identical or different, each represent an unbranched or branched alkoxy radical containing 1 to 6 carbon atoms.

Still more particularly, the present invention relates to the products of general formula (I) in which Z represents a hydrogen atom or a radical of general formula (II) in which $R_3$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ and $R_5$, which may be identical or different, each represent a methoxy, ethoxy or propoxy radical.

The products of general formula (I) in which Z represents a radical of general formula (II) display noteworthy antitumour and antileukaemic properties.

According to the present invention, the new products of general formula (I) in which Z represents a radical of general formula (II) may be obtained by esterification of a product of general formula (III):

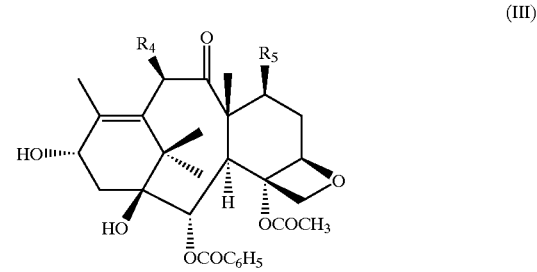

(III)

in which $R_4$ and $R_5$ are defined as above, by means of an acid of general formula (IV):

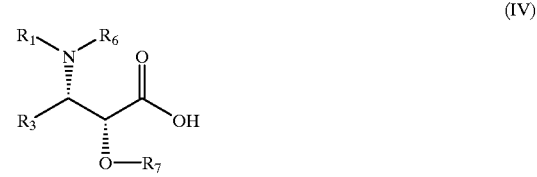

(IV)

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, or by means of a derivative of this acid, to obtain an ester of general formula (V):

(V)

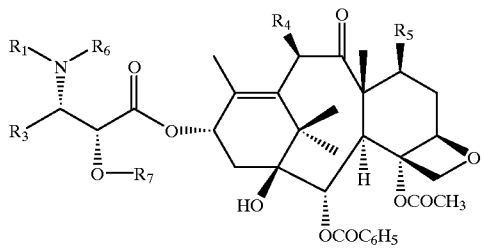

in which $R_1$, $R_3$, $R_4$, $R_5$, $R_6$ and $R_7$ are defined above, followed by replacement of the protective groups represented by $R_7$ and/or $R_6$ and $R_7$ by hydrogen atoms.

The esterification by means of an acid of general formula (IV) may be performed in the presence of a condensing agent (carbodiimide, reactive carbonate) and an activating agent (aminopyridines) in an organic solvent (ether, ester, ketones, nitriles, aliphatic hydrocarbons, halogenated aliphatic hydrocarbons, aromatic hydrocarbons) at a temperature from $-10$ to $90°$ C.

The esterification may also be carried out using the acid of general formula (IV) in the form of the symmetrical anhydride, working in the presence of an activating agent (aminopyridines) in an organic solvent (ethers, esters, ketones, nitriles, aliphatic hydrocarbons, halogenated aliphatic hydrocarbons, aromatic hydrocarbons) at a temperature of from 0 to $90°$ C.

The esterification may also be carried out using the acid of general formula (IV) in halide form or in the form of a mixed anhydride with an aliphatic or aromatic acid, optionally prepared in situ, in presence of a base (tertiary aliphatic amine), working in an organic solvent (ethers, ester, ketones, nitriles, aliphatic hydrocarbons, halogenated aliphatic hydrocarbons, aromatic hydrocarbons) at a temperature of from 0 to $80°$ C.

Preferably, $R_6$ represents a hydrogen atom and $R_7$ represents a group protecting the hydroxyl function, or alternatively $R_6$ and $R_7$ together form a saturated 5- or 6-membered heterocycle.

When $R_6$ represents a hydrogen atom, $R_7$ preferably represents a methoxymethyl, 1-ethoxyethyl, benzyloxymethyl, trimethylsilyl, triethylsilyl, β-trimethylsilylethoxymethyl, benzyloxycarbonyl or tetrahydropyranyl radical.

When $R_6$ and $R_7$ together form a heterocycle, the latter is preferably an oxazolidine ring optionally monosubstituted or gem-disubstituted at position 2.

Replacement of the protective groups $R_7$ and/or $R_6$ and $R_7$ by hydrogen atoms may be performed, depending on their nature, in the following manner:

1) when $R_8$ represents a hydrogen atom and $R_7$ represents a group protecting the hydroxyl function, replacement of the protective groups by hydrogen atoms is performed by means of an inorganic acid (hydrochloric acid, sulphuric acid, hydrofluoric acid) or organic acid (acetic acid, methanesulphonic acid, trifluoromethanesulphonic acid, p-toluenesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of from $-10$ to $60°$ C., or by means of a source of fluoride ions such as a hydrofluorine acid/triethylamine complex, or by catalytic hydrogenation, 2) when $R_6$ and $R_7$ together form a saturated 5- or 6-membered heterocycle, and more especially an oxazolidine ring of general formula (VI):

(VI)

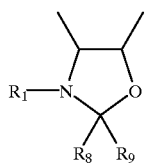

in which $R_1$ is defined as above and $R_8$ and $R_9$, which may be identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$, together with the carbon atom to which they are linked, form a 4- to 7-membered ring, replacement of the protective group formed by $R_6$ and $R_7$ by hydrogen atoms may be performed, depending on the meanings of $R_1$, $R_8$ and $R_9$, in the following manner:

a) when $R_1$ represents a tert-butoxycarbonyl radical and $R_8$ $R_9$, which may be identical or different, represent an alkyl radical or an aralkyl (benzyl) or aryl (phenyl) radical, or alternatively $R_6$ represents a trihalomethyl radical or a phenyl radical substituted with a trihalomethyl radical and $R_9$ represents a hydrogen atom, or alternatively $R_8$ and $R_9$ together form a 4- to 7-membered ring, treatment of the ester of general formula (v) with an inorganic or organic acid, where appropriate in an organic solvent such as an alcohol, yield the product of general formula (VII):

(VII)

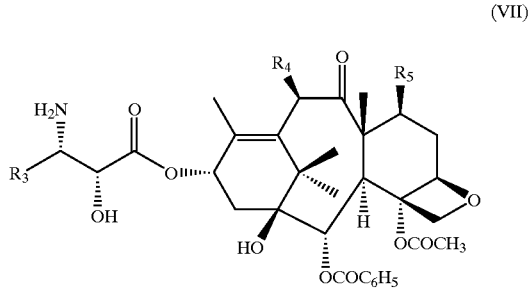

in which $R_3$, $R_4$ and $R_5$ are defined as above, which is acylated by means of benzoyl chloride in which the phenyl ring is optionally substituted or by means of thenoyl chloride, or furoyl chloride or of a product of general formula:

$$R_2-O-CO-X \qquad (VIII)$$

in which $R_2$ is defined as above and X represents a halogen atom (fluorine, chloride) or a residue $-O-R_2$ or —O—CO—O—R$_2$, to obtain a product of general formula (I) in which Z represents a radical of general formula (II).

Preferably, the product of general formula (V) is treated with formic acid at a temperature in the region of 20° C. to yield the product of general formula (VII).

Preferably, the acylation of the product of general formula (VII) by means of a benzoyl chloride in which the phenyl radical is optionally substituted or by means of thenoyl chloride, of furoyl chloride or of a product of general formula (VIII) is performed in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is performed at a temperature of from 0 to 50° C., and preferably at about 20° C.

b) wherein R$_1$ represents an optionally substituted benzoyl radical, a thenoyl or furoyl radical or a radical R$_2$O—CO— in which R$_2$ is defined as above, R$_8$ represents a hydrogen atom or an alkoxy radical containing 1 to 4 carbon atoms or a phenyl radical substituted with one or more alkoxy radicals containing 1 to 4 carbon atoms and R$_9$ represents a hydrogen atom, replacement of the protective group formed by R$_6$ and R$_7$ by hydrogen atoms is performed in the presence of an inorganic acid (hydrochloric acid, sulphuric acid) or organic acid (acetic acid, methanesulphonic acid, trifluoromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of from −10 to 60° C., and preferably from 15 to 30° C.

According to the invention, the products of general formula (III), that is to say the products of general formula (I) in which Z represents a hydrogen atom and R$_4$ and R$_5$ are defined as above, may be obtained from 10-deacetylbaccatin III of formula (IX):

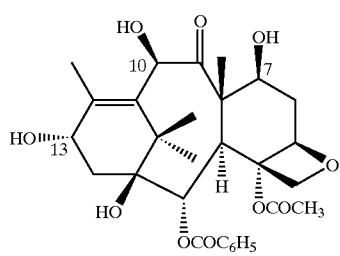

(IX)

It can be especially advantageous to protect the hydroxyl functions at the positions 7 and 13 selectively, for example in the form of a silyl diether which may be obtained by the action of a silyl halide of general formula:

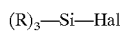

(X)

in which the symbols R$_1$ which may be identical or different, represent an alkyl radical containing 1 to 6 carbon atoms, optionally substituted with a phenyl radical, or a cycloalkyl radical containing 3 to 6 carbon atoms or a phenyl radical, on 10-deacetylbaccatin III, to obtain a product of general formula (XI):

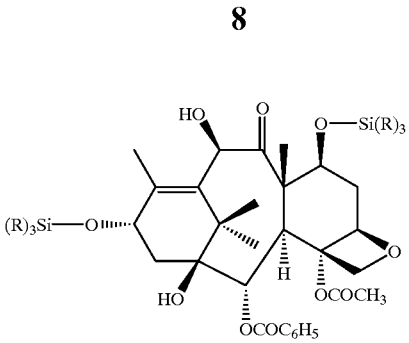

(XI)

in which R is defined as above, followed by the action of a product of general formula:

(XII)

in which R'$_4$ represents a radical such that R'$_4$—O is identical to R$_4$ defined as above and X$_1$ represents a reactive ester residue such as a sulphuric or sulphonic ester residue or a halogen atom, to obtain a product of general formula (XIII):

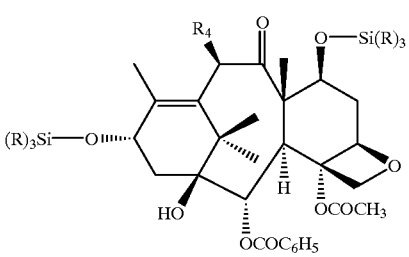

(XIII)

in which R and R$_4$ are defined as above, the silyl protective groups of which are replaced by hydrogen atoms to obtain a product of general formula (XIV):

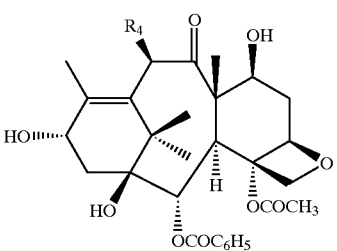

(XIV)

in which R$_4$ is defined as above, which is etherified selectively at position 7 by the action of a product of general formula:

(XV)

in which R'$_5$ represents a radical such that R'$_5$—O is identical to R$_5$ defined as above and X$_2$ represents a halogen atom or a reactive ester residue such as a sulphuric or sulphonic ester residue, to give the product of general formula (III).

Generally, the action of a silyl derivative of general formula (X) on 10-deacetylbaccatin III is performed in pyridine or triethylamine, where appropriate in the presence of an organic solvent such as an aromatic hydrocarbon, for instance benzene, toluene or xylenes, at a temperature between 0° C. and the refluxing temperature of the reaction mixture.

Generally, the action of a product of general formula (XII) on a product of general formula (XI) is performed, after metalation of the hydroxyl function at position 10 by means of an alkali metal hydride, such as sodium hydride, an alkali metal amide, such as lithium amide, or an alkali metal alkylide, such as butyllithium, working in an organic solvent, such as dimethylformamide or tetrahydrofuran, at a temperature of from 0 to 50° C.

Generally, the replacement of the silyl protective groups of the product of general formula (XIII) by hydrogen atoms is performed by means of an acid such as hydrofluoric acid or trifluoroacetic acid in the presence of a base such as triethylamine or pyridine optionally substituted with one or more alkyl radicals containing 1 to 4 carbon atoms, the base optionally being combined with an inert organic solvent such as a nitrile, for instance acetonitrile, or a halogenated aliphatic hydrocarbon, such as dichloromethane, at a temperature of from 0 to 80° C.

Generally, the action of a product of general formula (XV) on a product of general formula (XIV) is performed under the conditions described above for the action of a product of general formula (XII) on a product of general formula (XI).

According to the invention, the products of general formula (I) in which Z represents a radical of general formula (II), $R_4$ is defined as above and $R_5$ is defined as above may be obtained from a product of general formula (XVI):

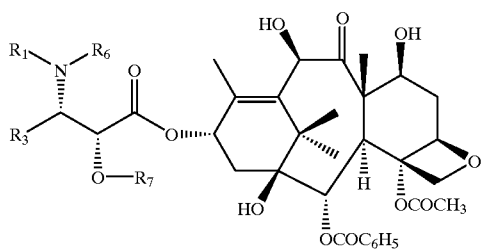

(XVI)

in which $R_1$, $R_3$, $R_6$ and $R_7$ are defined as above, by silylation at position 7 by means of a product of general formula (X), to obtain a product of general formula (XVII):

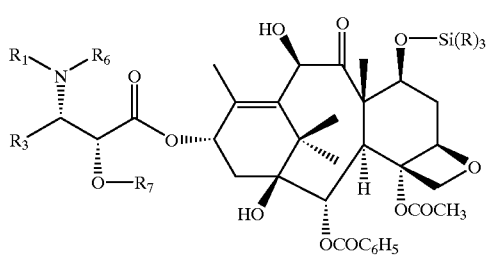

(XVII)

in which R, $R_1$, $R_3$, $R_6$ and $R_7$ are defined as above, which is functionalized at position 10 by means of a product of general formula (XII) to give a product of general formula (XVIII):

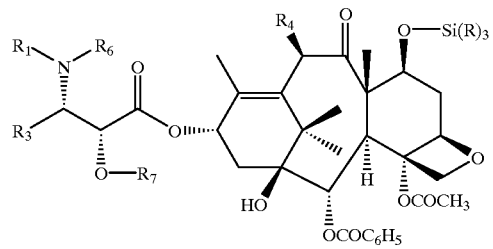

(XVIII)

in which R, $R_1$, $R_3$, $R_4$, $R_6$ and $R_7$ are defined as above, the silyl protective group of which is replaced by a hydrogen atom to give a product of general formula (XIX):

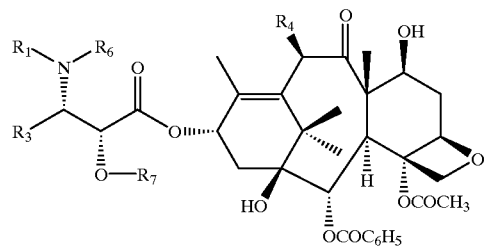

(XIX)

which, by the action of a product of general formula (XV), yields the product of general formula (V), the protective groups of which are replaced by hydrogen atoms to give a product of general formula (I) in which Z represents a radical of general formula (II).

The reactions used for silylation, functionalization and replacement of the protective groups by hydrogen atoms are performed under conditions similar to those described above.

The products of general formula (XVI) may be obtained under the conditions described in European Patent EP 0,336, 841 and international Applications PCT WO 92/09589 and WO 94/07878, the disclosures of which are hereby incorporated by reference in their entirety, or from the products of general formula (XX):

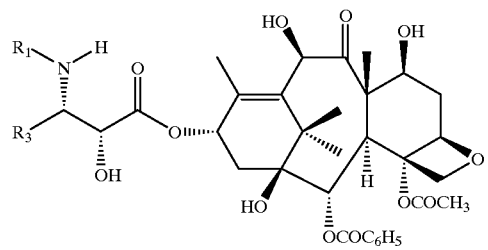

(XX)

in which $R_1$ and $R_3$ are defined as above, according to known methods for protecting the hydroxyl function of the side chain without affecting the remainder of the molecule.

According to the invention, the products of general formula (I) in which Z represents a hydrogen atom or a radical of general formula (II) may be obtained by the action of activated Raney nickel, in the presence of an aliphatic alcohol containing 1 to 3 carbon atoms or an ether such as tetrahydrofuran or dioxane, on a product of general formula (XXI):

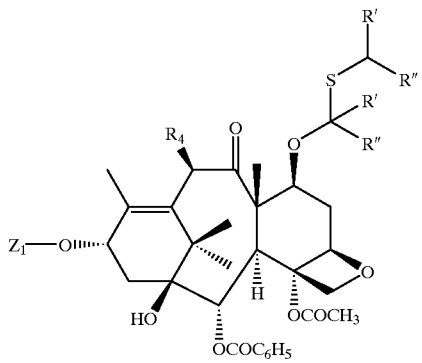

(XXI)

in which $R_4$ is defined as above and R' and R", which may be identical or different, represent a hydrogen atom or an alkyl radical containing 1 to 6 carbon atoms, an alkenyl radical containing 2 to 6 carbon atoms, an alkynyl radical containing 2 to 6 carbon atoms, a cycloalkyl radical containing 3 to 6 carbon atoms or a cycloalkenyl radical containing 3 to 6 carbon atoms, optionally substituted, or alternatively R' and R", together with the carbon atom to which they are linked, form a cycloalkyl radical containing 3 to 6 carbon atoms or a cycloalkenyl radical containing 4 to 6 carbon atoms, and $Z_1$ represents a hydrogen atom or a radical of general formula (XXII):

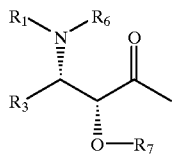

(XXII)

in which $R_1$, $R_3$, $R_6$ and $R_7$ are defined as above, and, to obtain a product of general formula (XXIII):

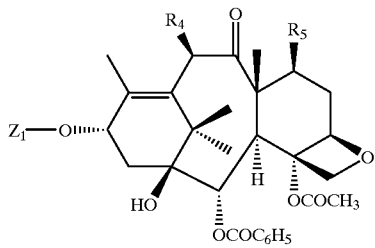

(XXIII)

followed, when $Z_1$ represents a radical of general formula (XXII), that is to say when the product of general formula (XXIII) is identical to the product of general formula (V), by replacement of the protective groups represented by $R_6$ and/or $R_6$ and $R_7$ by hydrogen atoms under the conditions described above.

Generally, the action of activated Raney nickel in the presence of an aliphatic alcohol or an ether is performed at a temperature of from −10 to 60° C.

According to the invention, the product of general formula (XXI) in which $Z_1$ and $R_4$ are defined as above may be obtained by the action of a sulphoxide of general formula (XXIV):

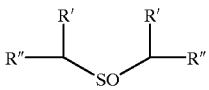

(XXIV)

in which R' and R" are defined as above, on a product of general formula (XIX).

Generally, the reaction of the sulphoxide of general formula (XXIV), preferably dimethyl sulphoxide, with the product of general formula (XIX) is performed in the presence of a mixture of acetic acid and acetic anhydride or a derivative of acetic acid such as a haloacetic acid at a temperature of from 0° to 50° C., and preferably at about 25° C.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules to tubulin is performed according to the method of G. Chauvière et al., C. R. Acad. Sci., 293, series II, 501–503 (1981). In this study, the products of general formula (I) in which Z represents a radical of general formula (II) were shown to be at least as active as taxol and Taxotere.

In vivo, the products of general formula (I) in which Z represents a radical of general formula (II) were shown to be active in mice grafted with B16 melanoma at doses of from 1 to 30 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The examples which follow illustrate the present invention.

EXAMPLE 1

126 mg of dicyclohexylcarbodiimide and then 14 mg of 4-(N,N-dimethylamino)pyridine were added successively at a temperature in the region of 20° C. to a suspension containing 217.8 mg of 4α-acetoxy-2α-benzoyloxy-5β,20-epoxy-1β,13α-dihydroxy-7β,10β-dimethoxy-9-oxo-11-taxene, 200 mg of (2R,4S,5R)-3-tert-butoxycarbonyl-2-(4-methoxyphenyl)-4-phenyl-1,3-oxazolidine-5-carboxylic acid and 50 mg of powdered 4 Å molecular sieve in 2 cm³ of ethyl acetate. The suspension obtained was stirred at a temperature in the region of 20° C. under an argon atmosphere for 16 hours, and then concentrated to dryness under reduced pressure (0.27 kPa) at a temperature in the region of 40° C. The residue obtained was purified by chromatography at atmospheric pressure on 50 g of silica (0.063–0.2 mm) contained in a column 2 cm in diameter (elution gradient: ethyl acetate/dichloromethane from 10:90 to 40:60 by volume), collecting 10-cm³ fractions. Fractions containing only the desired product were pooled and concentrated to dryness under reduced pressure (0.27 kPa) at 40° C. for 2 hours. 271.8 mg of 4α-acetoxy-2α-benzoyloxy- 5β,20-epoxy-1β-hydroxy-7β,10β-dimethoxy-9-oxo-11-taxen-13α-yl (2R,4S,5R)-3-tert-butoxycarbonyl-2-(4-methoxyphenyl)-4-phenyl-1,3-oxazolidine-5-carboxylate were thereby obtained in the form of a white solid, the characteristics of which were as follows:

¹H NMR spectrum (400 MHz; CDCl₃ with a few drops of CD₃OD-d₄; chemical shifts δ in ppm; coupling constants J in Hz): 1.02 (s, 9H: C(CH₃)₃); 1.10 (s, 3H: CH₃); 1.17 (s, 3H: CH₃); 1.63 (s, 3H: CH₃); from 1.65 to 1.85 and 2.60 (2 mts, 1H each; CH₂ at position 6); 1.78 (unres. comp., 3H: CH₃); 2.02 and 2.15 (2 dd, J=14 and 9, 1H each: CH₂ at position 14); 2.14 (s, 3H: CH₃); 3.22 and 3.35 (2 s, 3H each: OCH₃); 3.64 (d, J=7, 1H: H at position 3); 3.73 (mt, 1H: H at position 7); 3.76 (s, 3H: ArOCH₃); 4.06 and 4.16 (2 d, J=8.5, 1H each; CH₂ at position 20); 4.53 (d, J=5, 1H: H at position 2'); 4.67 (s, 1H: H at position 10); 4.85 (broad d, J=10, 1H: H at position 5); 5.36 (mt, 1H: H at position 3'); 5.52 (d, J=7, 1H: H at position 2); 6.07 (mt, 1H: H at position 13); 6.33 (unres. comp., 1H: H at position 5'); 6.88 (d, J=8, 2H: aromatic H at the ortho position with respect to OCH₃); from 7.25 to 7.40 (mt, 7H: aromatic H at position 3' and aromatic H at the meta position with respect to OCH₃); 7.43 (t, J=7.5, 2H: OCOC₆H₅ H at the meta position); 7.58 (t, J=7.5, 1H: OCOC₆H₅ H at the para position); 7.96 (d, J=7.5, 2H: OCOC₆H₅ H at the ortho position).

A solution of 446.3 mg of 4α-acetoxy-2α-benzoyloxy-5β,20-epoxy-1β-hydroxy-7β,10β-dimethoxy-9-oxo-11-taxen-13α-yl (2R,4S,5R)-3-tert-butoxycarbonyl- 2-(4-methoxyphenyl)-4-phenyl-1,3-oxazolidine-5-carboxylate in 11.6 cm³ of a 0.1N solution of hydrogen chloride in ethanol was stirred constantly at a temperature in the region of 0° C. for 16 hours under an argon atmosphere. The reaction mixture was then diluted with 40 cm³ of dichloromethane and 5 cm³ of distilled water. After settling had taken place, the aqueous phase was separated and extracted with 5 cm³ of dichloromethane. The organic phases were combined, dried over magnesium sulphate, filtered through sintered glass and then concentrated to dryness under reduced pressure (0.27 kPa) at a temperature in the region of 40° C. 424.2 mg of a pale yellow solid were obtained, which product was purified by preparative thin-layer chromatography [12 Merck preparative silica gel 60F₂₅₄ plates, thickness 1 mm, application in solution in a methanol/dichloromethane (5.95 by volume) mixture, eluting with a methanol/dichloromethane (5:95 by volume) mixture]. After elution of the zone corresponding to the main product with a methanol/dichloromethane (15:85 by volume) mixture, filtration through sintered glass and evaporation of the solvents under reduced pressure (0.27 kPa) at a temperature in the region of 40° C., 126 mg of 4α-acetoxy-2α-benzoyloxy-5β,20-epoxy-1β-hydroxy-7β,10β-dimethoxy-9-oxo-11-taxen-13α-yl (2R, 3S)-3-tert-butoxycarbonylamino-2-hydroxy-3-phenylpropionate were obtained in the form of an ivory-coloured foam, the characteristics of which were as follows:

optical rotation [α]₂₀ᴰ=−32.9 (c=0.5; methanol)

¹H NMR spectrum (400 MHz, CDCl₃; chemical shifts δ in ppm; coupling constants J in Hz): 1.23 (s, 3H: CH₃); 1.25 (s, 3H: CH₃); 1.39 (s, 9H: C(CH₃)₃); 1.70 (s, 1H: OH at position 1); 1.75 (s, 3H: CH₃); 1.82 and 2.72 (2 mts, 1H each: CH₂ at position 6); 1.91 (s, 3H: CH₃); 2.31 (limiting AB, 2H: CH₂ at position 14); 2.39 (s, 3H: COCH₃); 3.33 and 3.48 (2 s, 3H each: OCH₃); 3.48 (mt, 1H: OH at position 2'); 3.85 (d, J=7, 1H: H 3); 3.88 (dd, J=11 and 7, 1H: H 7); 4.20 and 4.33 (2 d, J=8.5, 1H each: CH₂ at position 20); 4.65 (mt, 1H: H at position 2'); 4.83 (s, 1H: H at position 10); 5.00 (broad d, J=10, 1H: H at position 5); 5.30 (broad d, J=10, 1H: H at position 3'); 5.47 (d, J=10, 1H: CONH); 5.66 (d, J=7, 1H: H at position 2); 6.24 (broad t, J=9, 1H: H at position 13); from 7.30 to 7.50 (mt, 5H: aromatic H at position 3'); 7.52 (t, J=7.5, 2H: OCOC₆H₅ H at the meta position); 7.63 (t, J=7.5, 1H: OCOC₆H₅ H at the para position); 8.12 (d, J=7.5, 2H: OCOC₆H₅ H at the ortho position).

4α-Acetoxy-2α-benzoyloxy-5β,20-epoxy-1β,13α-dihydroxy-7β,10β-dimethoxy-9-oxo-11-taxene (or 7β,10β-dimethoxy-10-deacetoxybaccatin III) was prepared in the following manner:

86 mg of sodium hydride at a concentration of 50% by weight in liquid paraffin were added portionwise to a solution, maintained under an argon atmosphere, at a temperature in the region of 0° C., of 500 mg of 4α-acetoxy-2α-benzoyloxy-5β,20-epoxy-1β,7β,13α-trihydroxy-10β-methoxy- 9-oxo-11-taxene in 5 cm³ of iodomethane and 0.5 cm³ of dimethylformamide. After 45 minutes at a temperature in the region of 0° C., the reaction mixture was diluted with 50 cm³ of ethyl acetate and 8 cm³ of distilled water. After settling had taken place, the organic phase was separated and washed with twice 8 cm³ of distilled water and then 8 cm³ of saturated aqueous sodium chloride solution, dried over magnesium sulphate, filtered through sintered glass and concentrated to dryness under reduced pressure (0.27 kPa) at a temperature in the region of 40° C. 570 mg of a pale yellow solid were thereby obtained, which product was purified by chromatography at atmospheric pressure on 50 g of silica (0.063–0.2 mm) contained in a column 2.5 cm in diameter, eluting with a methanol/dichloromethane (2:98 by volume) mixture and collecting 10-cm³ fractions. Fractions containing only the desired product were pooled and concentrated to dryness under reduced pressure (0.27 kPa) at 40° C. for 2 hours. 380 mg of 4α-acetoxy-2α-benzoyloxy-5β,20-epoxy-1β,13α-dihydroxy-7β,10β-dimethoxy-9-oxo-11-taxene were thereby obtained in the form of a pale yellow solid, the characteristics of which were as follows:

¹H NMR spectrum (400 MHz; CDCl₃; with a few drops of CD₃OD-d₄; chemical shifts δ in ppm; coupling constants J in Hz): 1.03 (s, 3H: CH₃); 1.11 (s, 3H: CH₃); 1.65 (s, 3H: CH₃); 1.72 and 2.67 (2 mts, 1H each: CH₂ at position 6); 2.05 (s, 3H: CH₃); 2.21 (limiting AB, J=14 and 9, 2H: CH₂ at position 14); 2.25 (s, 3H: COCH₃); 3.26 and 3.40 (2 s, 3H each: OCH₃); 3.85 (d, J=7, 1H: H at position 3); 3.89 (dd, J=11 and 6.5, 1H: H at position 7); 4.12 and 4.25 (2 d, J=8.5, 1H each: CH₂ at position 20); 4.78 (broad t, J=9, 1H: H at position 13); 4.83 (s, 1H: H at position 10); 4.98 (broad d, J=10, 1H: H at position 5); 5.53 (d, J=7, 1H: H at position 2); 7.43 (t, J=7.5, 2H: OCOC₆H₅ H at the meta position); 7.56 (t, J=7.5, 1H: OCOC₆H₅ H at the para position); 8.05 (d, J=7.5, 2H: OCOC₆H₅ H at the ortho position).

4α-Acetoxy-2α-benzoyloxy-5β,20-epoxy-1β,7β,13α-trihydroxy-10β-methoxy-9-oxo-11-taxene (or 10β-methoxy-10-deacetoxybaccatin III) was prepared in the following manner:

50 cm³ of hydrogen fluoride/triethylamine complex (3HF.Et₃N) were added slowly to a solution, maintained under an argon atmosphere, at a temperature in the region of 0° C., of 3.62 g of 4α-acetoxy-2α-benzoyloxy-5β,20-epoxy-1β-hydroxy-10β-methoxy-9-oxo-7β,13α-bis(triethylsilyloxy)-11-taxene in 30 cm³ of dichloromethane. After 48 hours at a temperature in the region of 20° C., the reaction mixture was poured into a suspension of 100 cm³ of supersaturated aqueous sodium hydrogen carbonate solution maintained at a temperature in the region of 0° C. After settling had taken place, the aqueous phase was separated and re-extracted with three times 80 cm³ of dichloromethane and then twice 80 cm³ of ethyl acetate. The organic phases were combined, dried over magnesium sulphate, filtered through magnesium sulphate and concentrated to dryness under reduced pressure (0.27 kPa) at a temperature in the region of 40° C. 3.45 g of a yellow foam were thereby obtained, which product was purified by chromatography at atmospheric pressure on 150 g of silica (0.063–0.2 mm) contained in a column 3.5 cm in diameter, eluting with a methanol/dichloromethane (5:95 by volume) mixture and collecting 35-cm³ fractions. Fractions containing only the desired product were pooled and concentrated to dryness under reduced pressure (0.27 kPa) at 40° C. for 2 hours. 1.97 g of 4α-acetoxy-2α-benzoyloxy-5β,20-epoxy-1β,7β,13α-trihydroxy-10β-methoxy-9-oxo-11-taxene were thereby obtained in the form of a white solid, the characteristics of which were as follows:

¹H NMR spectrum (400 MHz; CDCl₃; chemical shifts δ in ppm; coupling constants J in Hz): 1.10 (s, 3H: CH₃); 1.19 (s, 3H: CH₃); 1.48 (d, J=8.5, 1H: OH at position 13); 1.70 (s, 3H: CH₃); 1.81 and 2.61 (2 mts, 1H each: CH₂ at position 6); 2.09 (d, J=5, 1H: OH at position 7); 2.11 (s, 3H: CH₃); 2.30 (s, 3H: COCH₃); 2.32 (d, J=9, 2H: CH₂ at position 14); 3.48 (s, 3H: OCH₃); 3.97 (d, J=7, 1H: H at position 3); 4.18 and 4.33 (2 d, J=8.5, 1H each: CH₂ at position 20); 4.31 (mt, 1H: H at position 7); 4.93 (mt, 1H: H at position 13); 4.99 (s, 1H: H at position 10); 5.01 (broad d, J=10, 1H: H at position 5); 5.66 (d, J=7, 1H: H at position 2); 7.49 (t, J=7.5, 2H: OCOC₆H₅ H at the meta position); 7.63 (t, J=7.5, 1H: OCOC₆H₅ H at the para position); 8.12 (d, J=7.5, 2H: OCOC₆H₅ H at the ortho position).

4α-Acetoxy-2α-benzoyloxy-5β,20-epoxy-1β-hydroxy-10β-methoxy-9-oxo-7β,13α-bis(triethylsilyloxy)-11-taxene (or 10β-methoxy-10-deacetoxy-7,13-bis(triethylsilyl)baccatin III) was prepared in the following manner:

375 mg of sodium hydride at a concentration of 50% by weight in liquid paraffin were added portionwise to a solution, maintained under an argon atmosphere, at a temperature in the region of 0° C., of 5 g of 4α-acetoxy-2α-benzoyloxy-5β,20-epoxy-1β,10β-dihydroxy-9-oxo-7β,13α-bis(triethylsilyloxy)-11-taxene in 25 cm³ of iodomethane. The solution was stirred constantly for 45 minutes at a temperature in the region of 0° C., and then for 5 hours 30 minutes at a temperature in the region of 20° C. The reaction mixture was cooled again to a temperature in the region of 0° C., and 125 mg of sodium hydride at a concentration of 50% by weight in liquid paraffin were added portionwise. After 1 hour at 20° C. and then 18 hours at 5° C., the reaction mixture was diluted by adding 50 cm³ of dichloromethane and poured into 50 cm³ of saturated aqueous ammonium chloride solution, and settling was allowed to take place. The aqueous phase was separated and extracted with twice 30 cm³ of dichloroemethane, and the organic phases were then combined, washed with 10 cm³ of distilled water, dried over magnesium sulphate, filtered through sintered glass and concentrated to dryness under reduced pressure (0.27 kPa) at a temperature in the region of 40° C. 5.15 g of a yellow foam were thereby obtained, which product was purified by chromatography at atmospheric pressure on 300 g of silica (0.063–0.2 mm) contained in a column 5 cm in diameter (elution gradient: ethyl acetate/dichloromethane from 0:100 to 10:90 by volume), collecting 30-cm³ fractions. Fractions containing only the desired product were pooled and concentrated to dryness under reduced pressure (0.27 kPa) at 40° C. for 2 hours. 3.62 g of 4α-acetoxy-2α-benzoyloxy-5β,20-epoxy-1β-hydroxy-10β-methoxy-9-oxo-7β,13α-bis(triethylsilyloxy)-11-taxene were thereby obtained in the form of a pale yellow foam, the characteristics of which were as follows:

¹H NMR spectrum (600 MHz; CDCl₃; chemical shifts δ in ppm; coupling constants J in Hz): 0.58 and 0.69 (2 mts, 6H each: ethyl CH₂); 0.97 and 1.04 (2 t, J=7.5, 9H each: ethyl CH₃); 1.15 (s, 3H: CH₃); 1.18 (s, 3H: CH₃); 1.58 (s, 1H: OH at position 1); 1.68 (s, 3H: CH₃); 1.89 and 2.48 (2 mts, 1H each: CH₂ at position 6); 2.04 (s, 3H: CH₃); 2.15 and 2.23 (2 dd, J=16 and 9, 1H each: CH₂ at position 14); 2.29 (s, 3H: COCH₃); 3.40 (s, 3H: OCH₃); 3.83 (d, J=7, 1H: H at position 13); 4.15 and 4.30 (2 d, J=8.5, 1H each: CH₂ at position 20); 4.43 (dd, J=11 and 7, 1H: H at position 7); 4.91 (s, 1H: H at position 10); 4.96 (broad d, J=10, 1H at position 5); 5.01 (broad t, J=9, 1H: H at position 13); 5.62 (d, J=7, 1H: H at position 2); 7.46 (t, J=7.5, 2H: OCOC₆H₅ H at the meta position); 7.60 (t, J=7.5, 1H: OCOC₆H₅ H at the para position); 8.09 (d, J=7.5, 2H: OCOC₆H₅ H at the ortho position).

4α-Acetoxy-2α-benzoyloxy-5β,20-epoxy-1β,10β-dihydroxy-9-oxo-7β,13α-bis(triethylsilyloxy)-11-taxene (or 10-deacetyl-7,13-bis(triethylsilyl)baccatin III) was prepared in the following manner:

10.8 cm³ of triethylsilyl chloride were added to a solution, maintained under an argon atmosphere, at a temperature in the region of 20° C., of 14 g of 4α-acetoxy-2α-benzoyloxy-5β,20-epoxy-1β,7β,10β,13α-tetrahydroxy-9-oxo-11-taxene (10-deacetylbaccatin III) in 50 cm³ of anhydrous pyridine. After 17 hours at a temperature in the region of 20° C., the reaction mixture was brought to a temperature in the region of 115° C. and 10.8 cm³ of triethylsilyl chloride were then added. After 3 hours 15 minutes at a temperature in the region of 115° C., the reaction mixture was brought back to a temperature in the region of 20° C. and diluted with 30 cm³ of ethyl acetate and 100 cm³ of distilled water. After settling took place, the aqueous phase was separated and extracted with twice 50 cm³ of ethyl acetate. The organic phases were combined, washed with 50 cm³ of saturated aqueous sodium chloride solution, dried over magnesium sulphate, filtered through sintered glass and then concentrated to dryness under reduced pressure (0.27 kPa) at a temperature in the region of 40° C. 63.1 g of a brown oil were thereby obtained, which product was purified by chromatography at atmospheric pressure on 800 g of silica (0.063–0.2 mm) contained in a column 7 cm in diameter (elution gradient: ethyl acetate/dichloromethane from 0.100 to 5.95 by volume), collecting 60-cm³ fractions. Fractions containing only the desired product were pooled and concentrated to dryness under reduced pressure (0.27 kPa) at 40° C. for 2 hours. 9.77 g of 4α-acetoxy-2α-benzoyloxy-5β,20-epoxy-1β,10β-dihydroxy-9-oxo-7β,13α-bis(triethylsilyloxy)-11-taxene were thereby obtained in the form of a cream-coloured foam, the characteristics of which were as follows:

¹H NMR spectrum (400 MHz; CDCl₃, chemical shifts δ in ppm; coupling constants J in Hz): 0.55 and 0.68 (2 mts, 6H each: ethyl CH₂); 0.94 and 1.03 (2 t, J=9.5, 9H each: ethyl CH₃); 1.08 (s, 3H: CH₃); 1.17 (s, 3H: CH₃); 1.58 (s, 1H: OH at position 1); 1.73 (s, 3H: CH₃); 1.91 and 2.57 (2 mts, 1H each: CH₂ at position 2); 2.04 (s, 3H: CH₃); 2.12 and 2.23 (2 dd, J=16 and 9, 1H each: CH₂ at position 14);

2.30 (s, 3H: COCH$_3$); 3.88 (d, J=7, 1H: H at position 3); 4.16 and 4.32 (2 d, J=8.5, 1H each: CH$_2$ position 20); 4.27 (d, J=1, 1H: OH at position 10); 4.40 (dd, J=11 and 7, 1H: H at position 7); 4.95 (broad d, J=10, 1H: H at position 5); 4.95 (mt, 1H: H at position 13): 5.16 (d, J=1, 1H: H at position 10); 5.60 (d, J=7, 1H: H at position 2); 7.46 (t, J=7.5, 2H: OCOC$_6$H$_5$ H at the meta position); 7.60 (t, J=7.5, 1H: OCOC$_6$H$_5$ H at the para position); 8.09 (d, J=7.5, 2H: OCOC$_6$H$_5$ H at the ortho position).

EXAMPLE 2

340 mg of 4α-acetoxy-2α-benzoyloxy-5β,20-epoxy-1β-hydroxy-7β,10β-dimethoxy-9oxo-11-taxen-13α-yl (2R, 4S, 5R)-3-tert-butoxycarbonyl-2-(4-methoxyphenyl)-4-phenyl-1,3-oxazolidine-5-carboxylate were dissolved in 8 cm$^3$ of a 0.1N ethanolic solution of hydrochloric acid containing 1% of water. The solution thereby obtained was stirred for 13 hours at a temperature in the region of 20° C. and then for 80 hours at 4° C., and 20 cm$^3$ of dichloromethane were added. The organic phase was separated after settling had taken place and washed successively with 3 times 5 cm$^3$ of saturated aqueous sodium hydrogen carbonate solution, dried over magnesium sulphate, filtered and concentrated to dryness under reduced pressure (2.7 kPa) at 40° C. 300 mg of a while foam were obtained, which product was purified by chromatography on silica gel deposited on plates [gel 1 mm thick, plates 20×20 cm, eluent: dichloromethane/methanol (95.5 by volume)] in 80-mg fractions (4 plates). After localization with UV rays of the zone corresponding to the adsorbed desired product, this zone was scraped off, and the silica collected was washed on sintered glass with 10 times 5 cm$^3$ of ethyl acetate. The filtrates were combined and concentrated to dryness under reduced pressure (2.7 kPa) at 40° C. A white foam was obtained, which was repurified according to the same technique [3 plates: 20×20×1 mm; eluent: dichloromethane/ethyl acetate (90:10 by volume)]. 205 mg of 4α-acetoxy-2α-benzoyloxy-5β,20-epoxy-1β-hydroxy-7β,10β-dimethoxy-9-oxo-11-taxen-13α-yl (2R, 3S)-3-tert-butoxycarbonylamino-2-hydroxy-3-phenylpropionate were thereby obtained in the form of a white foam, the characteristics of which were as follows:

optical rotation [α]$_D^{20}$=−33 (c=0.5; methanol).

$^1$H NMR spectrum (400 MHz; CDCl$_3$; chemical shifts δ in ppm; coupling constants J in Hz): 1.23 (s, 3H: —CH$_3$); 1.25 (s, 3H: —CH$_3$); 1.39 [s, 9H: —C(CH$_3$)$_3$]; 1.70 , (s, 1H; —OH at position 1); 1.75 (s, 3H: —CH$_3$); 1.82 and 2.72 (2 mts, 1H each: —CH$_2$ at position 6); 1.91 (s, 3H: —CH$_3$); 2.31 (limiting AB, 2H: —CH$_2$ at position 14); 2.39 (s, 3H: —COCH$_3$); 3.33 and 3.48 (2 s, 3H each: —OCH$_3$); 3.46 (mt, 1H: OH at position 2'); 3.85 (d, J=7, 1H: —H at position 3); 3.88 (dd, J=11 and 7, 1H at position 7); 4.20 and 4.33 (2 d, J=8.5, 1H each: —CH$_2$ at position 20); 4.65 (mt, 1H: —H at position 2'); 4.83 (s, 1H: —H at position 10); 5.00 (broad d, J=10, 1H: —H at position 5); 5.30 (broad d, J=10, 1H: —H at position 3'); 5.47 (d, J=10, 1H: —CONH—); 5.66 (d, J=7, 1H: —H at position 2); 6.24 (broad t, J=9, 1H: —H at position 13); from 7.30 to 7.50 (mt, 5H: —C$_6$H$_5$ at position 3'); 7.52 [t, J=7.5, 2H: —OCOC$_6$H$_5$ (—H at position 3 and H at position 5)]; 7.63 [t, J=7.5, 1H: —OCOC$_6$H$_5$ (—H at position 4)]; 8.12 [d, J=7.5, 2H: —OCOC$_6$H$_5$ (—H at position 2 and H at position 6)].

4α-Acetoxy-2α-benzoyloxy-5β,20-epoxy-1β-hydroxy-7β,10β-dimethoxy-9-oxo-11-taxen-13α-yl (2R, 4S, 5R)-3-tert-butoxycarbonyl-2-(4-methoxyphenyl)-4-phenyl-1,3-oxazolidine-5-carboxylate was prepared in the following manner:

100 cm$^3$ of an ethanolic suspension of activated nickel according to Raney (obtained from 80 cm$^3$ of the approximately 50% commercial aqueous suspension by successive washing, to a pH in the region of 7, with 15 times 100 cm$^3$ of distilled water and with 5 times 100 cm$^3$ of ethanol) were added at a temperature in the region of 20° C. to a solution, maintained under an argon atmosphere and kept stirring, of 1 g of 4α-acetoxy-2α-benzoyloxy-5β,20-epoxy-1β-hydroxy-7β,10β-bis(methylthiomethoxy)-9-oxo-11-taxen-13α-yl (2R, 4S, 5R)-3-tert-butoxycarbonyl-2-(4-methoxyphenyl)-4-phenyl-1,3-oxazolidine-5-carboxylate in 100 cm$^3$ of anhydrous ethanol. The reaction medium was kept stirring for 24 hours at a temperature in the region of 20° C. and then filtered through sintered glass. The sintered glass was washed with 4 times 80 cm$^3$ of ethanol, and the filtrates were combined and concentrated to dryness under reduced pressure (2.7 kPa) at 40° C. 710 mg of a yellow foam were obtained, which product was purified by chromatography on 60 g of silica (0.063–0.2 mm) contained in a column 2.5 cm in diameter [eluent: dichloromethane/ethyl acetate (90:10 by volume)], collecting 6-cm$^3$ fractions. Fractions containing only the desired product are pooled and concentrated to dryness under reduced pressure (2.7 kPa) at 40° C. 350 mg of 4α-acetoxy-2α-benzoyloxy-5β,20-epoxy-1β-hydroxy-7β,10β-dimethoxy-9-oxo-11-taxen-13α-yl (2R, 4S, 5R)-3-tert-butoxycarbonyl-2-(4-methoxyphenyl)-4-phenyl-1,3-oxazolidine-5-carboxylate were thereby obtained in the form of a white foam.

4α-Acetoxy-2α-benzoyloxy-5β,20-epoxy-1β-hydroxy-7β,10β-bis(methylthiomethoxy)-9-oxo-11-taxen-13α-yl (2R, 4S, 5R)-3-tert-butoxycarbonyl-2-(4-methoxy-phenyl)-4-phenyl-1,3-oxazolidine-5-carboxylate was prepared in the following manner:

2.3 cm$^3$ of acetic acid and 7.55 cm$^3$ of acetic anhydride were added at a temperature in the region of 20° C. to a solution, maintained under an argon atmosphere and kept stirring, of 3.1 g of 4α-acetoxy-2α-benzoyloxy-5β,20-epoxy-1β-7β, 10β-trihydroxy-9-oxo-11-taxen-13α-yl (2R, 4S, 5R)-3-tert-butoxycarbonyl-2-(4-methoxyphenyl)-4-phenyl-1,3-oxazolidine-5-carboxylate dissolved in 102 cm$^3$ of dimethyl sulphoxide. The reaction mixture was kept stirring for 7 days at a temperature in the region of 20° C., and then poured into a mixture of 500 cm$^3$ of distilled water and 250 cm$^3$ of dichloromethane. 30 cm$^3$ of saturated aqueous potassium carbonate solution was then added with efficient stirring to a pH in the region of 7. After 10 minutes of stirring, the organic phase was separated after settling had taken place and the aqueous phase was re-extracted with twice 250 cm$^3$ of dichloromethane. The organic phases were combined, washed with 250 cm$^3$ of distilled water, drive over magnesium sulphate, filtered and concentrated to dryness under reduced pressure (2.7 kPa) at 40° C. 5.2 g of a pale yellow oil were obtained, which product was purified by chromatography on 200 g of silica (0.063–0.4 mm) contained in a column 3 cm in diameter [eluent: dichloromethane/methanol (99:1 by volume)], collecting 50-cm$^3$ fractions. Fractions containing only the desired product were pooled and concentrated to dryness under reduced pressure (2.7 kPa) at 40° C. 1.25 g of 4α-acetoxy-2α-benzoyloxy-5β,20-epoxy-1β-hydroxy-7β,10β-bis (methylthiomethoxy)-9-oxo-11-taxen-13α-yl (2R, 4S, 5R)-3-tert-butoxycarbonyl-2-(4-methoxyphenyl)-4-phenyl-1,3-oxazolidine-5-carboxylate were thereby obtained in the form of a white foam.

4α-Acetoxy-2α-benzoyloxy-5β,20-epoxy-1β,7β,10β-trihydroxy-9-oxo-11-taxen-13α-yl (2R, 4S, 5R)-3-tert-butoxycarbonyl-2-(4-methoxyphenyl)-4-phenyl-1,3-oxazolidine-5-carboxylate was prepared in the following manner.

A solution of 5.1 g of 4α-acetoxy-2α-benzoyloxy-5β,20-epoxy-1β-hydroxy-9-oxo-7β,10β-bis(2,2,2-trichloroethoxycarbonyloxy)-11-taxen-13α-yl (2R, 4S, 5R)-3-tert-butoxycarbonyl-2-(4-methoxyphenyl)-4-phenyl-1,3-oxazolidine-5-carboxylate in a mixture of 100 cm$^3$ of methanol and 100 cm$^3$ of acetic acid was heated, with stirring and under an argon atmosphere, to a temperature in the region of 60° C., and 10 g of powdered zinc were then added. The reaction mixture was then stirred for 15 minutes at 60° C., thereafter cooled to a temperature in the region of 20° C. and filtered through sintered glass lined with Celite. The sintered glass was washed with twice 15 cm$^3$ of methanol. The filtrate was concentrated to dryness under reduced pressure (2.7 kPa) at a temperature in the region of 40° C. 50 cm$^3$ of ethyl acetate and 25 cm$^3$ of saturated aqueous sodium hydrogen carbonate solution were added to the residue. The organic phase was separated after settling had taken place and washed successively with 25 cm$^3$ of saturated aqueous sodium hydrogen carbonate solution and with 25 cm$^3$ of distilled water, then dried over magnesium sulphate, filtered through sintered glass and concentrated to dryness under reduced pressure (2.7 kPa) at 40° C. 3.1 g of 4α-acetoxy-2α-benzoyloxy-5β,20-epoxy-1β, 7β,10β-trihydroxy-9-oxo-11taxen-13α-yl (2R, 4S, 5R)-3-tert-butoxycarbonyl-2-(4-methoxyphenyl)-4-phenyl-1,3-oxazolidine-5-carboxylate were thereby obtained in the form of a white foam.

4α-Acetoxy-2α-benzoyloxy-5β,20-epoxy-1β-hydroxy-9-oxo-7β,10β-bis(2,2,2-trichloroethoxy-carbonyloxy)-11-taxen-13α-yl (2R, 4S, 5R)-3-tert-butoxy-carbonyl-2-(4-methoxyphenyl)-4-phenyl-1,3-oxazolidine-5-carboxylate was prepared under the conditions described in Patent WO 94/07878, the disclosure of which is specifically incorporated by reference herein.

EXAMPLE 3

76 mg of dicyclohexylcarbodiimide and then 8.5 mg of 4-(N,N-dimethylamino)pyridine were added successively at a temperature in the region of 20° C. to a suspension containing 135 mg of 4α-acetoxy-2α-benzoyloxy-5β,20-epoxy-10β-ethoxy-1β,13α-dihydroxy-7β-methoxy-9-oxo-11-taxene, 120 mg of (2R, 4S, 5R)-3-tert-butoxycarbonyl-2-(4-methoxyphenyl)-4-phenyl-1,3-oxazolidine-5-carboxylic acid and 50 mg of powdered 4 Å molecular sieve in 1 cm$^3$ of anhydrous toluene. The suspension obtained was stirred at a temperature in the region of 20° C. under an argon atmosphere for 1 hour, and then purified by direct application to a column for chromatography at atmospheric pressure on 30 g of silica (0.063–0.2 mm) contained in a column 2.5 cm in diameter (elution gradient: ethyl acetate/dichloromethane from 2.98 to 10:90 by volume), collecting 10-cm$^3$ fractions. Fractions containing only the desired product were pooled and concentrated to dryness under reduced pressure (2.7 kPa) at 40° C. for 2 hours. 320.6 mg of a white solid were thereby obtained, which product was purified by preparative thin-layer chromatography: 10 Merck preparative silica gel 60F$_{254}$ plates, thickness 0.5 mm, application in solution in dichloromethane, eluting with a methanol/dichloromethane (3.97 by volume) mixture. After elution of the zones corresponding to the main products with a methanol/dichloromethane (15.85 by volume) mixture, filtration through cotton wool and then evaporation of the solvents under reduced pressure (2.7 kPa) at a temperature in the region of 40° C., 47.7 mg of 4α-acetoxy-2α-benzoyloxy-5β,20epoxy-10β-ethoxy-1β,13α-dihydroxy-7β-methoxy-9-oxo-11-taxene were obtained in the form of a cream-coloured solid and 37 mg of 4α-acetoxy-2α-benzoyloxy-5β,20-epoxy-10β-ethoxy-1β-hydroxy-7β-methoxy-9-oxo-11-taxen-13α-yl (2R, 4S, 5R)-3-tert-butoxycarbonyl-2-(4-methoxyphenyl)-4-phenyl-1,3-oxazolidine-5-carboxylate were obtained in the form of a white foam, the characteristics of which 5-carboxylate product were as follows:

$^1$H NMR spectrum (600 MHz; CDCl$_3$; at a temperature of 333 K; chemical shifts δ in ppm; coupling constants J in Hz): 1.09 (s, 9H: C(CH$_3$)$_3$; 1.19 (s, 3H: CH$_3$); 1.27 (t, J=7, 3H: ethyl CH$_3$); 1.43 (s, 1H; OH at position 1); 1.62 (s, 3H: CH$_3$); 1.68 (s, 3H: CH$_3$); 1.77 and 2.63 (2 mts, 1H each: CH$_2$ at position 6); 1.86 (s, 3H: COCH$_3$); 2.13 and 2.22 (2 dd, J=16 and 9, 1H each: CH$_2$ at position 14); 3.27 (s, 3H: OCH$_3$); 3.45 and 3.68 (2 mts. 1H each: ethyl CH$_2$); 3.76 (d, J=7, 1H: H3); 3.81 (s, 3H: ArOCH$_3$); 3.85 (dd, J=11 and 7, 1H: H at position 7); 4.13 and 4.23 (2 d, J=8.5, 1H each: CH$_2$ at position 20); 4.58 (d, J=4.5, 1H: H at position 2'); 4.83 (s, 1H: H at position 10); 4.90 (broad d, J=10, 1H: H at position 5); 5.46 (d, J=4.5, 1H: H at position 3'); 5.60 (d, J=7 Hz, 1H: H2); 6.13 (broad t, J=9 Hz, 1H: H13); 6.38 (s, 1H: H5'); 6.92 (d, J=8.5, 2H: aromatic H at the ortho position with respect to OCH$_3$); from 7.30 to 7.50 (mt, 9H: aromatic H at position 3'-aromatic H at the meta position with respect of OCH$_3$ and OCOC$_6$H$_5$ H at the meta position); 7.59 (t, J=7.5, 1H: OCOC$_6$H$_5$ H at the para position); 8.03 (d, J=7.5, 2H: OCOC$_6$H$_5$ H at the ortho position).

A solution of 48 mg of 4α-acetoxy-2α-benzoyloxy-5β, 20-epoxy-10β-ethoxy-1β-hydroxy-7β-methoxy-9-oxo-11-taxen-13α-yl (2R, 4S, 5R)-3-tert-butoxycarbonyl-2-(4-methoxyphenyl)-4-phenyl-1,3-oxazolidine-5-carboxylate in 0.5 cm$^3$ of ethyl acetate and 0.004 cm$^3$ of concentrated 37% hydrochloric acid was kept stirring at a temperature in the region of 20° C. for 1.5 hours under an agon atmosphere. The reaction mixture was then purified by preparative thin-layer chromatography; application of the crude reaction mixture to 5 Merck preparative silica gel 60F$_{254}$ plates, thickness 0.5 mm, eluting with a methanol/dichloromethane (4:96 by volume) mixture. After elution of the zone corresponding to the main product with a methanol/dichloromethane (15:85 by volume) mixture, filtration through cotton wool and then evaporation of the solvents under reduced pressure (2.7 kPa) at a temperature in the region of 40° C., 28.5 mg of 4α-acetoxy-2α-benzoyloxy-5β,20-epoxy-10β-ethoxy-1β-hydroxy-7β-methoxy-9-oxo-11-taxen-13α-yl (2R, 3S)-3-tert-butoxycarbonylamino-2-hydroxy-3-phenylpropionate were obtained in the form of an ivory-coloured foam, the characteristics of which were as follows:

$^1$H NMR spectrum (400 MHz; CDCl$_3$; chemical shifts δ in ppm; coupling constants J in Hz): 1.22 (s, 3H: CH$_3$); 1.25 (s, 3H: CH$_3$); 1.32 (t, J=7, 3H: ethyl CH$_3$); 1.38 (s, 9H: C(CH$_3$)$_3$; 1.64 (s, 1H: OH at position 1); 1.73 (s, 3H: CH$_3$); 1.80 and 2.70 (2 mts, 1H each: CH$_2$ at position 6); 1.88 (s, 3H: CH$_3$); 2.30 (mt, 2H: CH$_2$ at position 14); 2.38 (s, 3H, COCH$_3$); 3.31 (s, 3H: OCH$_3$); 3.44 (unres. comp. 1H: OH at position 2'); 3.50 and 3.70 (2 mts, 1H, each: ethyl OCH$_2$); 3.84 (d, J=7.5, 1H: H at position 3); 3.87 (dd, J=11 and 6.5, 1H: H at position 7); 4.18 and 4.32 (2 d, J =8.5, 1H each: CH$_2$ at position 20); 4.64 (mt, 1H: H at position 2$^1$); 4.90 (s, 1H: H at position 10); 4.98 (broad, d, J=10, 1H: H at position 5); 5.28 (broad, d, J=10, 1H: H at position 3'); 5.42 (d, J=10, 1H: CONH); 5.64 (d, J=7.5, 1H: H at position 2); 6.22 (broad, t, J=9, 1H: H at position 13); from 7.25 to 7.45 (mt, 5H: aromatic H at position 3'); 7.50 (d, J=7.5, 2H: OCOC$_6$H$_5$ H at the meta position); 7.62 (t, J=7.5, 1H: OCOC$_6$H$_5$ H at the para position); 8.12 (d, J=7.5, 2H: OCOC$_6$H$_5$ H at the ortho position).

4α-Acetoxy-2α-benzoyloxy-5β,20-epoxy-10β-ethoxy-1β,13α-dihydroxy-7β-methoxy-9-oxo-11-taxene (or 10β-ethoxy-7β-methoxy-10-deacetoxybaccatin III) may be prepared in the following manner:

43 mg sodium hydride at a concentration of 50% by weight in liquid paraffin were added portionwise to a solution, maintained under an argon atmosphere, at a temperature in the region of 0° C., of 235 mg of 4α-acetoxy-2α-benzoyloxy-5β,20-epoxy-1β,7β,13α-trihydroxy-10β-ethoxy-9-oxo-11-taxene-2.5 cm³ of iodomethane and 1 cm³ of dimethylformamide. After 30 minutes at a temperature in the region of 0° C., the reaction mixture was diluted with 40 cm³ of ethyl acetate, 6 cm³ of distilled water and 8 cm³ of saturated aqueous ammonium chloride solution. After setting had taken place, the organic phase was separated and washed with three times 8 cm³ of distilled water and then 8 cm³ of saturated aqueous NaCl solution, dried over magnesium sulphate, filtered through sintered glass and concentrated to dryness under reduced pressure (2.7 kPa) at a temperature in the region of 40° C. 268 mg of a yellow solid were thereby obtained, which product was purified by chromatography at atmospheric pressure on 30 g of silica (0.063–0.2 mm) contained in a column 2.5 cm in diameter (elution gradient: ethyl acetate/dichloromethane from 0:100 to 15.85 by volume), collecting 10-cm³ fractions. Fractions containing only the desired product were pooled and concentrated to dryness under reduced pressure (0.27 kPa) at 40° C. for 2 hours. 380 mg of 4α-acetoxy-2α-benzoyloxy-5β,20-epoxy-10β-ethoxy-1β,13α-dihydroxy-7β-methoxy-9-oxo-11-taxene are thereby obtained in the form of a white powder, the characteristic of which were as follows:

¹H NMR spectrum (300 MHz; CDCl₃ with the addition of a few drops of CD₃OD-d₄; chemical shifts δ in ppm, coupling constants J in Hz): 0.99 (s, 3H: CH₃); 1.09 (s, 3H; CH₃); 1.22 (t, J=7, 3H: ethyl CH₃); 1.62 (s, 3H: CH₃); 1.68 and 2.66 (2 mts, 1H each: CH₂6); 2.03 (s, 3H, CH₃); 2.13 and 2.22 (2 dd, J =16 and 9, 1H each: CH₂ at position 14); 2.23 (s, 3H: COCH₃); 3.23 (s, 3H: OCH₃); from 3.40 to 3.65 (mt, 2H; ethyl CH₂); 3.84 (d, J=7.5, 1H: H at position 3); 3.88 (dd, J=10 and 6.5, 1H: H at position 7); 4.10 and 4.23 (2 d, J=8.5, 1H each: CH₂2O); 4.75 (broad t, J=9, 1H: H at position 13); 4.90 (s, 1H: H at position 10); 4.97 (broad d, J=10, 1H: H at position 5); 5.51 (d, J=7.5, 1H: H at position 2); 7.42 (t, J=7.5, 2H: OCOC₆H₅ H at the meta position); 7.53 (t, J=7.5, 1H: OCOC₆H₅ at the para position); 8.03 (d, J=7.5, 2H: OCOC₆H₅ H at the ortho position).

4α-Acetoxy-2α-benzoyloxy-5β,20-epoxy-1β,7β,13α-trihydroxy-10β-ethoxy-9-oxo-11-taxene (or 10β-ethoxy-10-deacetoxybaccatin III) was prepared in the following manner:

9 cm³ of hydrogen fluoride/triethylamine (3HF.ET₃N) were added to a solution, maintained under an argon atmosphere, at a temperature in the region of 20° C., of 591 mg of 4α-acetoxy-2α-benzoyloxy-5β,20-epoxy-1β, hydroxy-10β-ethoxy-9-oxo-7β,13α-bis (triethylsilyloxy)-11-taxene in 6 cm³ of dichloromethane. After 21 hours at a temperature in the region of 20° C., the reaction mixture was diluted with 40 cm³ of dichloromethane and poured into a suspension of 40 cm³ of supersaturated aqueous sodium hydrogen carbonate solution maintained at a temperature in the region of 0° C. After dilution with 10 cm³ distilled water and when setting had taken place, the aqueous phase was separated and re-extracted with twice 20 cm³ of diethyl ether. The organic phases were combined, washed with 20 cm³ of distilled water and 20 cm³ of saturated aqueous sodium chloride solution, dried over magnesium sulphate, filtered through magnesium sulphate and concentrated to dryness under reduced pressure (2.7 kPa) at a temperature in the region of 40° C. 370 mg of a pale yellow foam were thereby obtained, which product is purified by chromatography at atmospheric pressure on 35 g of silica (0.0632–0.2 mm) contained in a column 2.5 cm in diameter, elutin with a methanol/dichloromethane (2:98 by volume) mixture and collecting 15-cm³ fractions. Fractions containing only the desired product were pooled and concentration to dryness under reduced pressure (2.7 kPa) at 40° C. for 2 hours. 236.2 mg of 4α-acetoxy-2α-benzoyloxy-5β,20-epoxy-1β,7β,13α-trihydroxy-10β-ethoxy-9-oxo-11-taxene were thereby obtained in the form of a white solid, the characteristics of which were as follows:

¹H NMR spectrum (400 MHz; CDCl₃: chemical shifts δ in ppm, coupling constants J in Hz): 1.08 (s, 3H: CH₃); 1.19 (s, 3H: CH₃); 1.29 (t, J=7.5, 3H: ethyl CH₃); 1.38 (d, J=9, 1H: OH at position 7); 1.59 (s, 1H: OH at position 1); 1.69 (s, 3H: CH₃); 1.82 and 2.62 (2 mts, 1H each: CH₂ at position 6); 2.02 (d, J=5, 1H: OH at position 13); 2.08 (s, 3H: CH₃); 2.30 (s, 3H: COCH₃); 2.32 (d, J=9, 2H: CH₂ at position 14); 3.56 and 3.67 (2 mts, 1H each: ethyl OCH₂); 3.98 (d, J=7, 1H: H at position 3); 4.18 and 4.33 (2 d, J=8.5 Hz, 1H each: CH₂2O); 4.30 (mt, 1H: H7); 4.90 (mt, 1H: H at position 13); 4.99 (dd, J=10 and 1.5, 1H: at position 5); 5.05 (s, 1H: H at position 10); 5.66 (d, J=7, 1H: H at position 2); 7.49 (t, J=7.5, 2H: OCOC₆H₅ H at the meta position); 7.63 (t, J=7.5, 1H: OCOC₆H₅ H at the para position); 8.12 (d, J=7.5, 2H: OCOC₆H₅ H at the ortho position).

4α-Acetoxy-2α-benzoyloxy-5β, 20-epoxy-1β-hydroxy-10β-ethoxy-9-oxo7β, 13α-bis(triethylsilyloxy)-11-taxene (or 10β-ethoxy-10-deacetoxy-7,13-bis(triethylsilyl)baccatin III) was prepared in the following manner:

93 mg of sodium hydride at a concentration of 50% by weight of liquid paraffin were added portionwise to a solution, maintained under an argon atmosphere, at a temperature in the region of 20° C., of 1 g of 4α-acetoxy-2α-benzoyloxy-5β,20-epoxy-1β, 10β-dihydroxy-9-oxo-7β, 13α-bis(triethylsilyloxy)-11-taxene in 3 cm³ of iodoethane and 4 cm³ of dimethylformamide. The solution was kept stirring for 17 hours at a temperature in the region of 20° C., and 93 mg of sodium hydride at a concentration of 50% by weight in liquid paraffin was then added portionwise. After 50 minutes at a temperature in the region of 20° C., the reaction mixture was diluted with 100 cm³ of ethyl acetate and 10 cm³ of saturated aqueous ammonium chloride solution. The organic phase was separated after settling had taken place and washed with six times 10 cm³ of distilled water and then 10 cm³ of saturated aqueous sodium chloride solution, dried over magnesium sulphate, filtered through sintered glass and concentrated to dryness under reduced pressure (2.7 kPa) at a temperature in the region of 40° C. 1.2 g of a yellow foam were thereby obtained, which product was purified by chromatography at atmospheric pressure on 150 g of silica (0.063–0.2 mm) contained in a column 3.5 cm in diameter, eluting with an ethyl acetate/dichloromethane (2.98, then 5.95 by volume) mixture and collecting 15-cm³ fractions. Fractions containing only the desired products were pooled and concentrated to dryness under reduced pressure (0.27 kPa) at 40° C. for 2 hours. 379.2 mg of 4α-acetoxy-2α-benzoyloxy-5β,20-epoxy-1β,10β-dihydroxy-9-oxo-7β, 13α-bis(triethylsilyloxy)-11-taxene were thereby obtained in the form of a pale yellow foam and 430 mg of 4α-acetoxy-2α-benzoyloxy-5β, 20-expoxy-1β-hydroxy-1β-ethoxy-9-oxo-7β, 13α-bis(triethylsilyloxy-11-taxene were thereby obtained in the form of a white foam, the characteristics of which 10-β-ethoxy product were as follows:

¹H NMR spectrum (400 MHz; CDCl₃, chemical shifts δ in ppm, coupling constant J in Hz): 0.57 and 0.70 (2 mts, 6H each; ethyl CH₂); 0.97 and 1.03 (2 t, J=7.5, 9H each: ethyl CH₃): 1.13 (s, 3H: CH₃): 1.20 (s, 3H: CH₃); 1.29 (t, J=7.5, 3H: CH₃ of ethoxy at position 10); 1.58 (s, 1H: OH at position 1); 1.66 (s, 3H: CH₃); 1.89 and 2.58 (2 mts, 1H each: CH₂ at position 2); 2.03 (s, 3H: CH₃); 2.13 and 2.23 (2 dd, J=16 and 9, 1H each: CH₂ at position 14); 2.30 (s, 3H: COCH₃); 3.53 (mt, 2H: CH₂ of ethoxy at position 10); 3.84 (d, J=7, 1H: H at position 3); 4.14 and 4.30 (2 d, J=8.5, 1H each: CH₂ at position 20); 4.43 (dd, J=11 and 6.5, 1H: H at position 7); from 4.90 to 5.00 (mt, 2H: H at position 13 and H at position 5); 5.01 (s, 1H, H at position 10); 5.61 (d, J=7, 1H: at position 2); 7.48 (t, J=7.5, 2H: OCOC₆H₅ H at the meta position); 7.61 (t, J=7.5, 1H: OCOC₆H₅ H at the para position); 8.10 (d, J=7.5, 2H: OCOC₆H₅ H at the ortho position).

EXAMPLE 4

65 mg of dicyclohexylcarbodiimide and then 7 mg of 4-(N,N-dimethylaminopyridine were added successively at a temperature in the region of 20° C. to a suspension containing 115 mg of 4α-acetoxy-2α-benzoyloxy-5β,20-epoxy-10β-(1-propyl)oxy-1β, 13α-dihydroxy-7β-methoxy-9-oxo-11-taxene and 100 mg of (2R,4S,5R)-3-tert-butoxycarbonyl-2-(4-methoxyphenyl-4-phenyl-1,3-oxazolidine-5-carboxylic acid in 1 cm³ of anhydrous toluene. The suspension obtained was stirred at a temperature in the region of 20° C. under an argon atmosphere for 1 hour, and then purified by direct application to a column for chromatography at atmospheric pressure on 30 g of silica (0.063–0.2 mm) contained in a column 2.5 cm in diameter (elution gradient: ethyl acetate/dichloromethane from 2.98 to 10:90 by volume), collecting 10-cm³ fractions. Fractions containing only the desired product were pooled and concentrated to dryness under reduced pressure (2.7 kPa) at 40° C. for 2 hours. 276.2 mg of a white solid were thereby obtained, which product was purified by reparative thin-layer chromatography: 10 Merck preparative silica gel 60F₂₅₄ plates, thickness 0.5 mm, application in solution in dichloromethane, eluting with a methanol/dichloromethane (3:97 volume) mixture. After elution of the zones corresponding to the main products with a methanol/dichloromethane (15:85 by volume) mixture, filtration through cotton wool and then evaporation of the solvents under reduced pressure (2.7 kPa) at a temperature in the region of 40° C., 84.8 mg of 4α-acetoxy-2α-benzoyloxy-5β,20-epoxy-10β-(1-propyl)oxy-1β-hydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate were obtained in the form of a white foam, the characteristics of which were as follows:

¹H NMR spectrum (300 MHz; CDCl₃; chemical shifts δ in ppm; coupling constants J in Hz): 0.97 (t, J=7, 3H: propyl CH₃) 1.07 (s, 9H: C(CH₃)₃); 1.19 (s, 6H: CH₃); from 1.50 to 1.80 (mt, 3H: OH at position 1 and central CH₂ of propyl); 1.60 (s, 3H: CH₃); 1.70 (s, 3H: CH₃); 1.78 and 2.63 (2 mts, 1H each: CH₂ at position 6); 1.82 (unres. comp. 3H: COCH₃); 2.07 and 2.19 (2 dd, J=16 and 9, 1H each: CH₂ at postion 14); 3.26 (s, 3H: OCH₃); 3.30 and 3.58 (2 mts, 1H each: propyl OCH₂); 3.73 (d, J=7.5, 1H: H at position 3); 3.81 (s, 3H: ArOCH₃); 3.81 (mt, 1H: H at position 7); 4.09 and 4.23 (2 d, J=8.5, 1H each: CH₂ at position 20); 4.57 (d, J=4.5, 1H: H at position 2'); 4.79 (s, 1H: H at position 10); 4.90 (broad d, J=10, 1H: H at position 5); 5.40 (unres. comp. 1H: H at position 3'); 5.58 (d, J=7.5, 1H: H at position 2); 6.13 (broad t, J=9, 1H: H at position 13); 6.40 (spread unres. comp. 1H: H at position 5'); 6.92 (d, J=8.5, 2H: aromatic H at the ortho position with respect to OCH₃); from 7.30 to 7.60 (mt, 9H: aromatic H at position 3'-aromatic H at the meta position with respect to OCH₃ and OCOC₆H₅ meta H); 7.63 (t, J=7.5, 1H: OCOC₆H₅ H at the para position); 8.03 (d, J=7.5, 2H: OCOC₆H₅ at the ortho position).

4α-Acetoxy-2α-benzoyloxy-5β,20-epoxy-1β-(1-propyl)oxy-1β-hydroxy-7β-methoxy-9-oxo-11-taxen-13α-yl (2R,3S)-3-tert-butoxycarbonylamino-2-hydroxy-3-phenylpropionate was prepared in the following manner:

A solution of 84 mg of 4α-acetoxy-2α-benzoyloxy-5β, 20-expoxy-10β-(1-propyl)oxy-1β-hydroxy-7β-methoxy-9-oxo-11-taxen-13α-yl (2R,4S,5R)-3-tert-butoxy-carbonyl-2-(4-methoxyphenyl)-4-phenyl-1,3-oxazolidine-5-carboxylate in 0.84 cm³ of ethyl acetate and 0.0071 cm³ of concentrated 37% hydrochloric acid was kept stirring at a temperature in the region of 20° C. for 1 hour under an argon atmosphere. The reaction mixture was then purified by preparative thin-layer chromatography: application of the crude reaction mixture to 6 Merck preparative silica gel 60F₂₅₄ plates, thickness 0.5 mm, eluting with a methanol/acetonitrile/dichloromethane (3:7:90 by volume) mixture. After elution of the zone corresponding to the main product with a methanol/dichloromethane (15:85 by volume) mixture, filtration through cotton wool and then evaporation of the solvents under reduced pressure (2.7 kPa) at a temperature in the region of 40° C., 27 mg of 4α-acetoxy-2α-benzoyloxy-5β,20-epoxy-10β-(1-propyl)oxy-1β-hydroxy-7β-methoxy-9-oxo-11-taxen-13α-yl (2R,3S)-3-tert-butoxycarbonylamino-2-hydroxy-3-phenyl-propionate were obtained in the form a white foam, the characteristics of which are as follows:

¹H NMR spectrum (400 MHz; CDCl₃; chemical shifts δ in ppm; coupling constants J in Hz);: 0.99 (t, J=7, 3H: propyl CH₃); 1.22 (s, 3H: CH₃); 1.25 (s, 3H: CH₃); 1.38 (s, 9H: C(CH₃)₃; 1.64 (s, 1H: OH at position 1); 1.69 (mt, 2H: central CH₂ of propyl): 1.73 (s, 3H: CH₃); 1.80 and 2.70 (2 mts, 1H each: CH₂ at position 6); 1.88 (s, 3H: CH₃); 2.30 (mt, 2H: CH₂ at position 14); 2.38 (s, 3H: COCH₃); 3.31 (s, 3H: OCH₃); 3.36 and 3.64 (2 mts, 1H each: propyl OCH₂); 3.44 (unres. comp. 1H: OH at position 2'); 3.84 (d, J=7.5, Hz, 1H: at position 3); 3.87 (dd, J=11 and 6.5, 1H: H at position 7); 4.18 and 4.30 (2 d, J=8.5, 1H each: CH₂ at position 20); 4.64 (mt, 1H: H at position 2'); 4.89 (s, 1H: H at position 10); 4.98 (broad d, J=10, 1H: H at position 5); 5.28 (broad d, J=10, 1H: H at position 3'); 5.42 (d, J=10, 1H: CONH); 5.64 (d, J=7.5, 1H: H at position 2): 6.22 (broad t, J=9, 1H: H at position 13); from 7.25 to 7.45 (mt, 5H: aromatic H at position 3'); 7.50 (d, J=7.5, 2H: OCOC₆H₅ H at the meta position); 7.61 (t, J=7.5, 1H: OCOC₆H₅ H at the para position); 8.12 (d, J=7.5, 2H: OCOC₆H₅ H at the ortho position).

4α-Acetoxy-2α-benzoyloxy-5β, 20-epoxy-10β-(1-propyl)oxy-1β, 13α-dihydroxy-7β-methoxy-9-oxo-11-taxene (or 10β-(1-propyl)oxy-7β-methoxy-10-deacetoxybaccatin III) was prepared in the following manner:

30 mg of sodium hydride at a concentration of 50% by weight in liquid paraffin were added portionwise to a solution, maintained under an argon atmosphere, at a temperature in the region of 0° C., of 165 mg of 4α-acetoxy-2α-benzoyloxy-5β,20-epoxy-1β,7β,13α-trihydroxy-10β-(1-propyl)oxy-9-11-taxene in 1.7 cm³ of iodomethane and 1 cm³ of dimethylformamide. After 30 minutes at a temperature in the region of 0° C., the reaction mixture was diluted with 40 cm³ of ethyl acetate, 5 cm³ of distilled water and 7 cm³ of saturated aqueous ammonium chloride solution. After settling had taken place, the organic phase was separated and washed with three times 7 cm³ of distilled water and then 7 cm³ of saturated aqueous sodium chloride solution, dried over magnesium sulphate, filtered through sintered glass and concentrated to dryness under reduced pressure (2.7 kPa) at a temperature in the region of 40° C., 224 mg of the yellow solid were thereby obtained, which product was purified by chromatography at atmospheric pressure on 20 g of silica (0.063–2 mm) contained in column 2.5 cm in diameter (elution gradient: ethyl acetate/dichloromethane from 0.100 to 15.85 by volume), collecting 10-cm³ fractions. Fractions containing only the desired product were pooled and concentrated to dryness under reduced pressure (2.7 kPa) at 40° C. for 2 hours. 117.5 mg of 4α-acetoxy-2α-benzoyloxy-5β,20-epoxy-10β-(1-propyl)oxy-1β,13α-dihydroxy-7β-methoxy-9-oxo-11-taxene were thereby obtained in the form of a white foam, the characteristics of which were as follows:

¹H NMR spectrum (300 MHz; CDCl₃; chemical shifts δ ppm, coupling constants J in Hz): 0.98 (t, J=7, 3H: propyl CH₃); 1.05 (s, 3H: CH₃); 1.19 (s, 3H: CH₃); from 1.60 to 1.80 (mt, 2H: central CH₂ of propyl); from 1.65 to 1.85 and 2.66 (2 mts, 1H each; CH₂ at position 6 ); 1.72 (s, 3H: CH₃); 2.10 (s, 3H: CH₃): from 2.05 to 2.35 (mt, 2H: cH₂ at position 14); 2.28 (s, 3H: COCH₃); 3.32 (s, 3H: OCH₃); 3.45 and 3.65 (2 mts, 1H each: propyl OCH₂); 3.92 (d, J=7.5, 1H: H3); 3.93 (dd, J=11 and 6, 1H: H at position 7); 4.16 and 4.32 (2 d, J=8.5, 1H each: CH₂ at position 20); 4.90 (mt, 1H: H at position 13); 4.94 (s, 1H: H at position 10); 5.03 (broad d, J=10, 1H: H at position 5); 5.60 (d, J=7.5, 1H: H at position 2); 7.48 (t, J=7.5, 2H: OCOC₆H₅ H at the meta position); 7.62 (t, J=7.5, 1H: OCOC₆H₅ H at the para position); 8.11 (d, J=7.5, 2H: OCOC₆H₅ at the ortho position).

4α-Acetoxy-2α-benzoyloxy-5β, 20-epoxy-1β,7β,13α-trihydroxy-10β-(1-propyl)oxy-9-oxo-11-taxene (or 10β-(1-propyl)oxy-10-deacetoxybaccatin III) was prepared in the following manner:

8.75 cm³ of hydrogen fluoride/triethylamine complex (3HF, Et₃N) were added to a solution, maintained under an argon atmosphere, at a temperature in the region of 20° C., of 585 mg of 4α-acetoxy-2α-benzoyloxy-5β,20-epoxy-1β-hydroxy-10β-(1-propyl)oxy-9-7β,13α-bis(triethylsilyloxy)-11-taxene in 6 cm³ of dichloromethane. After 24 hours at a temperature in the region of 20° C., the reaction mixture was diluted with 30 cm³ of dichloromethane and poured into a suspension of 30 cm³ of supersaturated aqueous sodium hydrogen carbonate solution maintained at a temperature in the region of 0° C. After dilution with 10 cm³ of distilled water and when settling had taken place, the aqueous phase was separated and re-extracted with twice 20 cm³ of diethyl ether. The organic phases were combined, washed with 20 cm³ of distilled water and 20 cm³ of saturated aqueous sodium chloride solution, dried over magnesium sulphate, filtered through magnesium sulphate and concentrated to dryness under reduced pressure (2.7 kPa) at a temperature in the region of 40° C. 500 mg of a pale yellow foam were thereby obtained, which product was purified by chromatography at atmospheric pressure on 40 g of silica (0.063–0.2 mm) contained in a column 2.5 cm in diameter, eluting with a methanol/dichloromethane (2:98 by volume) mixture and collecting 15-cm³ fractions. Fractions containing only the desired product were pooled and concentrated to dryness under reduced pressure (2.7 kPa) at 40° C. for 2 hours. 373.8 mg of 4α-acetoxy-2α-benzoyloxy-5β,20-expoxy-1β,7β,13α-trihydroxy-10β-(1-propyl)oxy-9-oxo-11-taxene were thereby obtained in the form of a white solid, the characteristics of which were as follows:

¹H NMR spectrum (300 MHz: CDCl₃; chemical shifts 67 in ppm, coupling constants J in Hz): 0.95 (t, J=7, 3H: propyl CH₃); 1.06 (s, 3H: CH₃); 1.22 (s, 3H: CH₃); 1.45 (d, J=7.5, 1H: OH at position 7); from 1.60 to 1.80 (mt, 2H: central CH₂ of propyl); 1.67 (s, 3H: CH₃); 1.83 and 2.62 (2 mts, 1H each: CH₂ at position 6); 2.05 (s, 3H: CH₃); 2.05 (mt, 1H: OH at position 13); 2.27 (limiting AB, 2H: CH₂ at position 4); 2.28 (s, 3H: COCH₃); 3.40 and 3.57 (2 mts, 1H each: propyl OCH₂); 3.97 (d, J=7.5, 1H: H at position 3); 4.15 and 4.30 (2 d, J=8.5, 1H each: CH₂ at position 20); 4.28 (mt, 1H: H at position 7); 4.90 (mt, 1H: H at position 13); 4.98 (broad d, J=10, 1H: H at position 5); 5.03 (s, 1H: H at position 10); 5.65 (d, J=7.5, 1H: H at position 2); 7.50 (t, J=7.5, 2H: OCOC₆H₅ at the meta position); 7.60 (t, J=7.5, 1H: OCOC₆H₅ H at the para position); 8.00 (d, J=7.5, 2H: OCOC₆H₅ H at the ortho position).

4α-Acetoxy-2α-benzoyloxy-5β,20-expoxy-1β-hydroxy-10β-(1-propyl)oxy-9-oxo-7β,13α-bis(triethyl-silyloxy)-11-taxene (or 10β-(1-propyl)oxy-10-deacetoxy-7,13-bis(triethylsilyl)baccatin III) was prepared in the following manner:

93 mg of sodium hydride at a concentration of 50% by weight in liquid paraffin were added portionwise to a solution, maintained under an argon atmosphere, at a temperature in the region of 20° C., of 1 g of 4α-acetoxy-2α-benzoyloxy-5β,20-expoxy-1β,10β-dihydroxy-9-oxo-7β, 13α-bis(triethylsilyoxy)-11-taxene in 3 cm³ of iodoethane and 4 cm³ of dimethylformamide. The solution was kept stirring for 19 hours at a temperature in the region of 20° C., and 93 mg of sodium hydride at a concentration of 50% by weight in liquid paraffin were then added portionwise. After 3 hours at a temperature in the region of 20° C., the reaction mixture was diluted with 100 cm³ of ethyl acetate and 10 cm³ of saturated aqueous ammonium chloride solution. The organic phase was separated after settling had taken place and washed with six times 10 cm³ of distilled water and then 10 cm³ of saturated aqueous sodium chloride solution, dried over magnesium sulphate, filtered through sintered glass and concentrated to dryness under reduced pressure (2.7 kPa) at a temperature in the region of 40° C., 1.32 g of a pale yellow foam were thereby obtained, which product was purified by chromatography at atmospheric pressure on 150 g of silica (0.063–0.2 mm) contained in a column 3.5 cm in diameter, eluting with an ethyl acetate/dichloromethane (2:98, then 5:95 by volume) mixture and collection 15-cm³ fractions. Fractions containing only the desired products were pooled and concentrated to dryness under reduced pressure (0.27 kPa) at 40° C. for 2 hours. 376.3 mg of 4α-acetoxy-2α-benzoyloxy-5β,20-expoxy-1β,10β-dihydroxy-9-oxo-7β,13α-bis(triethylislyoxy)-11-taxene were thereby obtained in the form of a pale yellow foam and 395.3 mg of 4α-acetoxy-2α-benzoyloxy-5β,20-expoxy-1β-hydroxy-10β-(1-propyl)oxy-9-oxo-7β,13α-bis(triethylsilyloxy)-11-taxene were thereby obtained in the form of a pale yellow foam, the characteristics of which were as follows:

¹H NMR spectrum (400 MHz; CDCl₃; chemical shifts δ in ppm; coupling constants J in Hz): 0.57 and 0.70 (2 mts, 6H each; ethyl CH₂): 0.94 and 1.03 (2 t, J=7.5, 9H each: ethyl CH₃); 0.94 (t, J=7.5, 3H: propyl CH₃); 1.14 (s, 3H: CH₃); 1.21 (s, 3H: CH₃); 1.67 (s, 3H: CH₃); 1.69 (mt, 2H: central CH₂ of propyl); 1.88 and 2.48 (2 mts, 1H each: CH₂ at position 6); 2.03 (s, 3H: CH₃); 2.14 and 2.23 (2 dd, J=16 and 9, 1H each: CH₂ at position 14); 2.30 (s, 3H: COCH₃); 3.40 (mt, 2H: propyl OCH₂); 3.84 (d, J=7.5, 1H: H at position 3); 4.16 and 4.30 (2 d, J=8.5, 1H each: CH₂ at position 20); 4.44 (dd, J=11 and 6.5, 1H: H at position 7); 4.96 (broad d, J=10 Hz, 1H: H5); 4.97 (s, 1H: H 10); 4.99 (broad t, J=9 Hz, 1H: H at position 13); 5.62 (d, J=7.5, 1H: H at position 2); 7.48 (t, J=7.5, 2H: OCOC$_6$H$_5$ H at the meta position); 7.60 (t, J=7.5, 1H: OCOC$_6$H$_5$ H at the para position); 8.10 (d, J=7.5, 2H: OCOC$_6$H$_5$ H at the ortho position).

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilm's tumor, Hodgkin's disease, melanoma, multiple myeloma, chronic lymphocytic leukemia and acute or chronic granulocytic lymphoma.

The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferable the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspension, injectable solutions which can contain emulsifying agents, colourings, preservatives or stabilizers. However, the compositions can also take the form of tablets, pills, powders or granules which can be administered orally.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consists of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single does contains from 0.01 to 1000 mg approximately of active product for parental administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphoines and cytokines such as interleukins, interferons ($\alpha$, $\beta$ or $\delta$) and TNF.

Other chemotherapeutic agents which are useful in the treatment of disorders due to abnormal cell proliferation include, without implied limitation, alkylating agents, for instance nitrogen mustards such as mechlorethamine, chyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antibiotics such as dactinomycin, danuorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstiboestrol and ethylnyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation.

The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained.

For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses generally range form 0.01 to 200 mg/kg. For intraperitioneal administration, the doses will generally range from 0.1 to 100 mg/kg, preferably from 0.5 to 50 mg/kg and still more specifically from 1 to 10 mg/kg. For intravenous administration, the doses generally range from 0.1 to 50 mg/kg, preferably from 0.1 to 5 mg/kg and still more specifically from 1 to 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ehtanol, and the solution is then diluted by adding 18 cm³ of physiological saline. The composition is administered by perfusion over 1 hour by introduction in physiological solution.

We claim:

1. A taxoid of the formula (I):

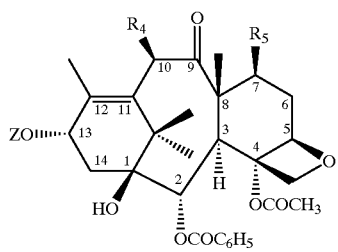

(I)

in which

Z represents a hydrogen atom or a radical of formula (II):

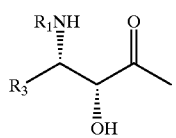

(II)

in which:

$R_1$ represents a benzoyl radical optionally substituted with one or more identical or different atoms or radicals selected from halogen atoms, alkyl radicals containing 1 to 4 carbon atoms, alkoxy radicals containing 1 to 4 carbon atoms, and trifluoromethyl radicals, a thenoyl radical, a furoyl radical, or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents selected from halogen atoms; hydroxyl radicals; alkoxy radicals containing 1 to 4 carbon atoms; dialkylamino radicals in which each alkyl portion contains 1 to 4 carbon atoms; piperidino radicals; morpholino radicals; 1-piperazinyl radicals optionally substituted at position 4 with an alkyl radical containing 1 to 4 carbon atoms or with a phenylalkyl radical in which the alkyl portion contains 1 to 4 carbon atoms; cycloalkyl radicals containing 3 to 6 carbon atoms; cycloalkenyl radicals containing 4 to 6 carbon atoms; phenyl radicals optionally substituted with one or more atoms or radicals selected from halogen atoms, alkyl radicals containing 1 to 4 carbon atoms and alkoxy radicals containing 1 to 4 carbon atoms; cyano radicals; carboxyl radicals; and alkoxycarbonyl radicals in which the alkyl portion contains 1 to 4 carbon atoms, a phenyl or α- or β-naphthyl radical optionally substituted with one or more atoms or radicals selected from halogen atoms; alkyl radicals containing 1 to 4 carbon atoms; and alkoxy radicals containing 1 to 4 carbon atoms, a 5-membered aromatic heterocyclic radical, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl on α- or β-naphthyl radical optionally substituted with one or more identical or different atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocyclic containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals, $R_4$ represents an alkoxy radical containing 1 to 6 carbon atoms in an unbranched or branched chain, and $R_5$ represents an alkoxy radical containing 1 to 6 carbon atoms in an unbranched or branched chain.

2. A taxoid according to claim 1, wherein Z represents a hydrogen atom or a radical of formula (II) in which $R_1$ represents a benzoyl radical or a radical $R_2$—O—CO— in which $R_2$ represents a tert-butyl radical, and $R_3$ represents an alkyl radical containing 1 to 6 carbon atoms, an alkenyl radical containing 2 to 6 carbon atoms; a cycloalkyl radical containing 3 to 6 carbon atoms; a phenyl radical optionally substituted with one or more identical or different atoms or radical selected from halogen atoms, alkyl, alkoxy, dialkylamino, acylamino, alkoxycarbonylamino and trifluoromethyl radicals, or a 2-furyl, 3- furyl, 2-thienyl, 3-thienyl, 2-thiazolyl, 4-thiazolyl, or 5-thiazolyl radical.

3. A taxoid according to claim 1, wherein Z represents a hydrogen atom or a radical of formula (II) in which $R_1$ represents a benzoyl radical or a radical $R_2$—O—CO— in which $R_2$ represents a tert-butyl radical, $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ and $R_5$, which may be identical or different, each represents a methoxy, ethoxy or propoxy radical.

4. A taxoid according to claim 1, wherein when $R_2$ represents a 5-membered aromatic heterocyclic radical, said radical is a furyl or thienyl radical.

5. 4α-acetoxy-2α-benzoyloxy-5β,20-epoxy-10β-ethoxy-1β-hydroxy-7β-methoxy-9-oxo-11-taxen-13α-yl(2R,3S)-3-tert-butoxycarbonylamino-2-hydroxy-3-phenylpropionate.

6. 4α-acetoxy-2α-benzoyloxy-5β,20-epoxy-10β-(1-propyl)oxy-1β-hydroxy-7β-methoxy-9-oxo-11-taxen-13α-yl(2R,3S)-3-tert-butoxycarbonylamino-2-hydroxy-3-phenyl-propionate.

7. A pharmaceutical composition comprising at least one product according to claim 1 wherein Z represents a radical formula (II), in combination with one or more pharmaceutically acceptable diluents or adjuvants and optionally one or more compatible and pharmacologically active compounds.

8. A pharmaceutical composition comprising at least the product according to claim 5 in combination with one or more pharmaceutically acceptable diluents or adjuvants and optionally one or more compatible and pharmacologically active compounds.

9. A pharmaceutical composition comprising at least the product according to claim 6 in combination with one or more pharmaceutically acceptable diluents or adjuvants and optionally one or more compatible and pharmacologically active compounds.

10. An ester of the formula (V):

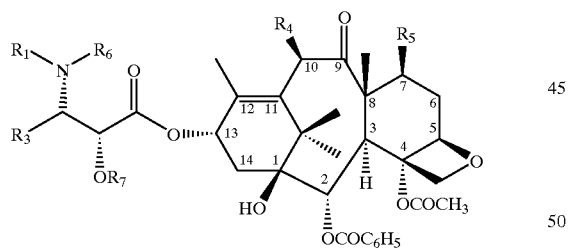

(V)

wherein $R_1$ represents a benzoyl radical optionally substituted with one or more identical or different atoms or radicals selected from halogen atoms, alkyl radicals containing 1 to 4 carbon atoms, alkoxy radicals containing 1 to 4 carbon atoms, and trifluoromethyl radicals, a thenoyl radical, a furoyl radical, or a radical $R_2$—O—CO— in which $R_2$ represents;

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents selected from halogen atoms; hydroxyl radicals; alkoxy radicals containing 1 to 4 carbon atoms; dialkylamino radicals in which each alkyl portion contains 1 to 4 carbon atoms; piperidino radicals; morpholino radicals; 1-piperazinyl radicals optionally substituted at position 4 with an alkyl radical containing 1 to 4 carbon atoms or with a phenylalkyl radical in which the alkyl portion contains 1 to 4 carbon atoms; cycloalkyl radicals containing 3 to 6 carbon atoms; cycloalkenyl radicals containing 4 to 6 carbon atoms; phenyl radicals optionally substituted with one or more atoms or radicals selected from halogen atoms, alkyl radicals containing 1 to 4 carbon atoms and alkoxy radicals containing 1 to 4 carbon atoms; cyano radicals; carboxyl radicals; and alkoxycarbonyl radicals in which the alkyl portion contains 1 to 4 carbon atoms, a phenyl or α- or β-naphthyl radical optionally substituted with one or more atoms or radicals selected from halogen atoms; alkyl radicals containing 1 to 4 carbon atoms; and alkoxy radicals containing 1 to 4 carbon atoms, a 5-membered aromatic heterocyclic radical, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or or 5-membered aromatic heterocyclic containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals.

$R_4$ represents an alkoxy radical containing 1 to 6 carbon atoms in an unbranched or branched chain, $R_5$ represents an alkoxy radical containing 1 to 6 carbon atoms in an unbranched or branched chain, and either $R_6$ represents a hydrogen atom and $R_7$ represents a group protecting the hydroxyl function, or $R_6$ and $R_7$ together form a saturated 5- or 6-membered heterocycle.

11. An ester of formula (VII):

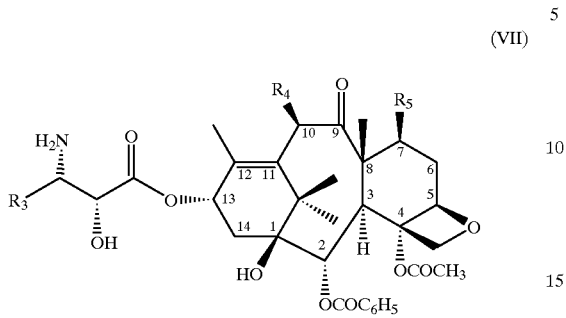

wherein

R₃ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio, hydroxyl, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulfur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the provision that, in the substituents of the phenyl, α- or β-naphthyl and aromatic heterocyclic radicals in the definitions of R₂ and R₃, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals, R₄ represents an alkoxy radical containing 1 to 6 carbon atoms in an unbranched or branched chain, and R₅ represents an alkoxy radical containing 1 to 6 carbon atoms in an unbranched or branched chain.

12. 4α-Acetoxy-2α-benzoyloxy-5β,20-epoxy-1β-hydroxy-7β,10β-bis(methylthiomethoxy)-9-oxo-11-taxen-13α-yl(2R,4S,5R)-3-tert-butoxycarbonyl-2-(4-methoxyphenyl)-4-phenyl-1,3-oxazolidine-5-carboxylate.

13. A taxoid of the formula (I):

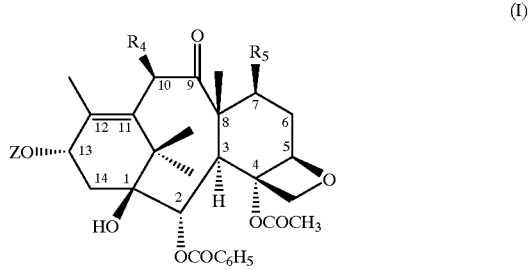

in which:
Z represents a hydrogen atom or a radical of formula (II):

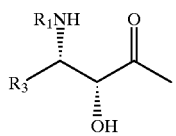

in which:
R₁ represents a benzoyl radical optionally substituted with one or more identical or different atoms or radicals selected from halogen atoms, alkyl radicals containing 1 to 4 carbon atoms, alkoxy radicals containing 1 to 4 carbon atoms, and trifluoromethyl radicals,
a thenoyl radical,
a furoyl radical, or
a radical R₂—O—CO— in which R₂ represents:
an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with or more substituents selected from halogen atoms; hydroxyl radicals; alkoxy radicals containing 1 to 4 carbon atoms; dialkylamino radicals in which each alkyl portion contains 1 to 4 carbon atoms; piperidino radicals; morpholino radicals; 1-piperazinyl radicals optionally substituted at position 4 with an alkyl radical containing 1 to 4 carbon atoms or with a phenylalkyl radical in which the alkyl portion contains 1 to 4 carbon atoms; cycloalkyl radicals containing 3 to 6 carbon atoms; cycloalkenyl radicals containing 4 to 6 carbon atoms; phenyl radicals optionally substituted with one or more atoms or radicals selected from halogen atoms, alkyl radicals containing 1 to 4 carbon atoms and alkoxy radicals containing 1 to 4 carbon atoms; cyano radicals; carboxyl radicals; and alkoxycarbonyl radicals in which the alkyl portion contains 1 to 4 carbon atoms.
a phenyl or α- or β-naphthyl radical optionally substituted with one or more atoms or radicals selected from halogen atoms; alkyl radicals containing 1 to 4 carbon atoms; and alkoxy radicals containing 1 to 4 carbon atoms,
a 5-membered aromatic heterocyclic radical, or
a saturated heterocyclic radical containing 4 to 6 carbon atoms, optionally substituted with one or more alkyl radicals containing 1 to 4 carbon atoms, R₃ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more identical or different atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hereto atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals, $R_4$ represents an alkoxy radical containing 1 to 6 carbon atoms in an unbranched or branched chain substituted with at least one substituent selected from an alkylthio radical containing 1 to 4 carbon atoms, and $R_5$ represents an alkoxy radical containing 1 to 6 carbon atoms in an unbranched or branched chain substituted with at least one substituent selected from an alkylthio radical containing 1 to 4 carbon atoms.

14. An ester of the formula (V):

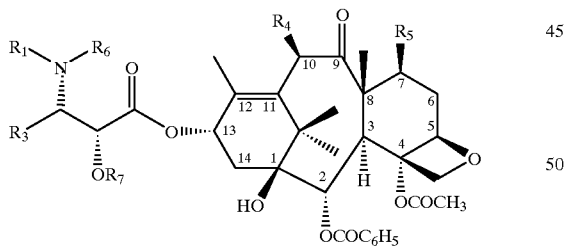

(V)

wherein $R_1$ represents a benzoyl radical optionally substituted with one or more identical or different atoms or radicals selected from halogen atoms, alkyl radicals containing 1 to 4 carbon atoms, alkoxy radicals containing 1 to 4 carbon atoms, and trifluoromethyl radicals, a thenoyl radical, a furoyl radical, or a radical $R_2$—O—CO— in which $R_2$ represents;

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents selected from halogen atoms; hydroxyl radicals; alkoxy radicals containing 1 to 4 carbon atoms; dialkylamino radicals in which each alkyl portion contains 1 to 4 carbon atoms; piperidino radicals; morpholino radicals; 1-piperazinyl radicals optionally substituted at position 4 with an alkyl radical containing 1 to 4 carbon atoms or with a phenylalkyl radical in which the alkyl portion contains 1 to 4 carbon atoms; cycloalkyl radicals containing 3 to 6 carbon atoms; cycloalkenyl radicals containing 4 to 6 carbon atoms; phenyl radicals optionally substituted with one or more atoms or radicals selected from halogen atoms, alkyl radicals containing 1 to 4 carbon atoms and alkoxy radicals containing 1 to 4 carbon atoms; cyano radicals; carboxyl radicals; and alkoxycarbonyl radicals in which the alkyl portion contains 1 to 4 carbon atoms, a phenyl or α- or β-naphthyl radical optionally substituted with one or more atoms or radicals selected from halogen atoms; alkyl radicals containing 1 to 4 carbon atoms; and alkoxy radicals containing 1 to 4 carbon atoms, a 5-membered aromatic heterocyclic radical, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl of α- or β-naphthyl radicals, $R_4$ represents an alkoxy radical containing 1 to 6 carbon atoms in an unbranched or branched chain substituted with at least one substituent selected from an alkylthio radical containing 1 to 4 carbon atoms, $R_5$ represents an alkoxy radical containing 1 to 6 carbon atoms in an unbranched or branched chain substituted with at least one substituent selected from an alkylthio radical containing 1 to 4 carbon atoms, and either $R_6$ represents a hydrogen atom and $R_7$ represents a group protecting the hydroxy function, or $R_5$ and $R_7$ together form a saturated 5- or 6-membered heterocycle.

15. An ester of formula (VII):

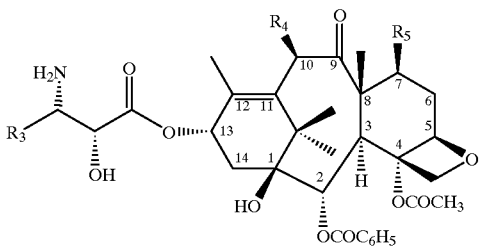

(VII)

wherein
$R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercaptor, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocyclic containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals $R_4$ represents an alkoxy radical containing 1 to 6 carbon atoms in an unbranched or branched chain substituted with at least one substituent selected from an alkylthio radical containing 1 to 4 carbon atoms, and $R_5$ represents an alkoxy containing 1 to 6 carbon atoms in an unbranched or branched chain substituted with at least one substituent selected from an alkylthio radical containing 1 to 4 carbon atoms.

16. A pharmaceutical composition according to claim 7, wherein said on or more compatible and pharmacologically active compounds is present and is cisplatin.

17. A pharmaceutical composition according to claim 16, wherein Z represents a radical of formula (II) in which
$R_1$ represents a benzoyl radical or a radical $R_2$—O—CO— in which $R_2$ represents a tert-butyl radical, and $R_3$ represents an alkyl radical containing 1 to 6 carbon atoms; an alkenyl radical containing 2 to 6 carbon atoms; a cycloalkyl radical containing 3 to 6 carbon atoms; a phenyl radical optionally substituted with one or more identical or different atoms or radicals selected from halogen atoms, alkyl, alkoxy, dialkylamino, acylamino, alkoxycarbonylamino and trifluoromethyl radicals; or a 2-furyl, 3-furyl, 2-thienyl, 3-thienyl, 2-thiazolyl, 4-thiazolyl, or 5-thiazolyl radical.

18. A pharmaceutical composition according to claim 17, wherein Z represents a radical of formula (II) in which
$R_1$ represents a benzoyl radical or a radical $R_2$—O—CO— in which $R_2$ represents tert-butyl radical, $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ and $R_5$, which may be identical or different, each represent a methoxy, ethoxy or propoxy radical.

19. A pharmaceutical composition according to claim 16, wherein when $R_2$ represents a 5-membered aromatic heterocyclic radical, said radical is a furyl or thienyl radical.

20. A pharmaceutical composition comprising 4α-acetoxy-2α-benzoyloxy-1β-hydroxy-5β,20-epoxy-7β,10β-dimethoxy-9-oxo-11-taxen-13α-yl(2R,3S)-3-tert-butoxycarbonylamino-2-hydroxy-3-phenylpropionate and cisplatin.

21. A pharmaceutical composition comprising 4α-acetoxy-2α-benzoyloxy-5β,20-epoxy-10β-ethoxy-1β-hydroxy-7β-methoxy-9-oxo-11-taxen-13α-yl(2R,3S)-3-phenylpropionate and cisplatin.

22. A pharmaceutical composition comprising 4α-acetoxy-2α-benzoyloxy-5β,20-epoxy-10β-(1-propyl)oxy-1β-hydroxy-7β-methoxy-9-oxo-11-taxen-13α-yl (2R,3S)-3-tert-butoxycarbonylamino-2-hydroxy-3-phenyl-propionate and cisplatin.

23. A pharmaceutical composition comprising 4α-acetoxy-2α-benzoyloxy-1β-hydroxy-5β,20-epoxy-7β,10β-dimethoxy-9-oxo-11-taxen-13α-yl(2R,3S)-3-tert-butoxycarbonylamino-2-hydroxy-3-phenylpropionate in combination with one or more pharmaceutically acceptable diluents or adjuvants and one or more compatible and pharmacologically active compounds.

24. A pharmaceutical composition comprising an ester of the formula (V):

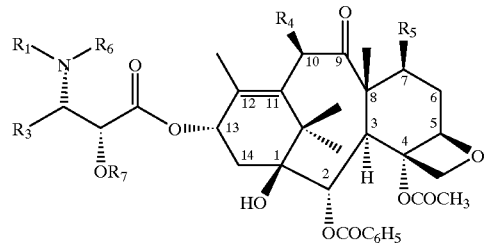

(V)

wherein
$R_1$ represents a benzoyl radical optionally substituted with one or more identical or different atoms or radicals selected from halogen atoms, alkyl radicals containing 1 to 4 carbon atoms, alkoxy radicals containing 1 to 4 carbon atoms, and trifluoromethyl radicals, a thenoyl radical, a furoyl radical, or a radical $R_2$—O—CO— in which $R_2$ represents an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents selected from halogen atoms; hydroxyl radicals; alkoxy radicals containing 1 to 4 carbon atoms; dialkylamino radicals in which each alkyl portion contains 1 to 4 carbon atoms; piperidino radicals; morpholino radicals; 1-piperazinyl radicals optionally substituted at position 4 with an alkyl radical containing 1 to 4 carbon atoms or with a phenylalkyl radicals in which the alkyl portion contains 1 to 4 carbon atoms; cycloalkyl radicals containing 3 to 6 carbon atoms; cycloalkenyl radicals containing 4 to 6 carbon atoms; phenyl radicals optionally substituted with one or more atoms or radicals selected from halogen atoms, alkyl radicals containing 1 to 4 carbon atoms and alkoxy radicals containing to 4 carbon atoms; cyano radicals; carboxyl radicals; and alkoxycarbonyl radicals in which the alkyl portion contains 1 to 4 carbon atoms, a phenyl or α- or β-naphthyl radical optionally substituted with one or more atoms or radicals selected from halogen atoms; alkyl radicals containing 1 to 4 carbon atoms; and alkoxy radicals containing 1 to 4 carbon atoms, a 5-membered aromatic heterocyclic radical, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, cycloalkyl radical containing 3 to 6 carbon atoms, a phenyl or α- or β-naphthyl radical optionally substituted with one or more atoms or radicals selected from halogen atoms, alkyl, alkenyl, alkynyl, aryl, aralkyl, alkoxy, alkylthio, aryloxy, arylthio, hydroxy hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulphur atoms and optionally substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals, with the proviso that, in the substituents of the phenyl, α- or β-naphthyl and aromatic heterocyclic radicals in the definitions of $R_2$ and $R_3$, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals, $R_4$ represents an alkoxy radical containing 1 to 6 carbon atoms in an unbranched or branched chain, $R_5$ represents an alkoxy radical containing 1 to 6 carbon atoms in an unbranched or branched chain, and $R_6$ and $R_7$ each represents a hydrogen atom in combination with one or more pharmaceutically acceptable diluents or adjuvants and one or more compatible and pharmacologically active compounds.

25. A pharmaceutical composition according to claim 24, wherein said one or more compatible and pharmacologically active compounds is cisplatin.

\* \* \* \* \*

UNITED STATES PATENT AND TRADEMARK OFFICE
CERTIFICATE OF CORRECTION

PATENT NO. : 6,331,635 B1
DATED : December 18, 2001
INVENTOR(S) : Hervé Bouchard et al.

It is certified that error appears in the above-identified patent and that said Letters Patent is hereby corrected as shown below:

Column 29,
Line 35, "in which" should read -- in which: --.

Column 30,
Line 26, "phenyl on" should read -- phenyl or --.
Line 36, "heterocyclic" should read -- heterocycle --.
Line 62, "atoms, an" should read -- atoms; an --.
Line 65, "radical" should read -- radicals --.

Column 31,
Line 1, "radicals," should read -- radicals; --.
Line 1, "3- furyl" should read -- 3-furyl --.
Lines 24 and 25, "radical formula" should read -- radical of formula --.
Line 62, "represents;" should read -- represents: --.

Column 32,
Line 43, "or 5-membered" should read -- a 5-membered --.
Line 43, "heterocyclic" should read -- heterocycle --.
Line 59, "radicals." should read -- radicals, --.

Column 33,
Line 33, delete "hydroxyl", second occurrence.
Line 42, "sulfur" should read -- sulphur --.
Line 50, "provision" should read -- proviso --.

Column 34,
Line 43, "with or" should read -- with one or --.
Line 58, "atoms." should read -- atoms, --.

Column 35,
Line 64, "represents;" should read -- represents: --.

Column 36,
Line 34, "atoms, cycloalkyl" should read -- atoms, a cycloalkyl --.
Line 39, "arylthio hydroxyl" should read -- arylthio, hydroxyl --.
Line 59, "phenyl of" should read -- phenyl or --.

UNITED STATES PATENT AND TRADEMARK OFFICE
CERTIFICATE OF CORRECTION

PATENT NO. : 6,331,635 B1
DATED : December 18, 2001
INVENTOR(S) : Hervé Bouchard et al.

It is certified that error appears in the above-identified patent and that said Letters Patent is hereby corrected as shown below:

Column 37,
Line 4, "$R_5$" should read -- $R_6$ --.
Line 31, "mercaptor" should read -- mercapto --.
Line 37, "heterocyclic" should read -- heterocycle --.
Line 62, "on or" should read -- one or --.

Column 38,
Line 13, "represents tert-butyl" should read -- represents a tert-butyl --.
Line 31, before "phenylpropionate", insert -- tert-butoxycarbonylamino-2-hydroxy-3- --.

Column 39,
Line 1, "represents" should read -- represents: --.
Line 15, "radicals" should read -- radical --.
Lines 21 and 22, "containing to" should read -- containing 1 to --.
Line 39, "atoms, cycloalkyl" should read -- atoms, a cycloalkyl --.

Column 40,
Line 4, "hydroxy" should read -- hydroxyl, --.

Signed and Sealed this

Ninth Day of March, 2004

JON W. DUDAS
*Acting Director of the United States Patent and Trademark Office*